US009662318B2

(12) United States Patent
Boulos

(10) Patent No.: US 9,662,318 B2
(45) Date of Patent: *May 30, 2017

(54) BITOPIC MUSCARINIC AGONISTS AND ANTAGONISTS AND METHODS OF SYNTHESIS AND USE THEREOF

(71) Applicant: BARRY UNIVERSITY, INC., Miami Shores, FL (US)

(72) Inventor: John Boulos, Miami Lakes, FL (US)

(73) Assignee: BARRY UNIVERSITY, INC., Miami Shores, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/005,203

(22) Filed: Jan. 25, 2016

(65) Prior Publication Data
US 2016/0136145 A1    May 19, 2016

Related U.S. Application Data

(63) Continuation-in-part of application No. 14/628,760, filed on Feb. 23, 2015, which is a continuation of
(Continued)

(51) Int. Cl.
*A61K 31/452* (2006.01)
*A61K 45/06* (2006.01)
(Continued)

(52) U.S. Cl.
CPC ........ *A61K 31/452* (2013.01); *A61K 31/4453* (2013.01); *A61K 45/06* (2013.01);
(Continued)

(58) Field of Classification Search
CPC .. A61K 31/452; A61K 45/06; A61K 31/4453; C07D 295/104; C07D 405/06; C07D 417/06
See application file for complete search history.

(56) References Cited

PUBLICATIONS

Rozengart et al. (Journal of Evolutionary Biochemistry and Physiology, vol. 45, No. 1. 2009).*

* cited by examiner

*Primary Examiner* — Savitha Rao
*Assistant Examiner* — Angela Brown-Pettigrew
(74) *Attorney, Agent, or Firm* — Fox Rothschild LLP

(57) ABSTRACT

Compositions for treating a condition associated with activity of a muscarinic receptor (e.g., one or more of $M_1$, $M_2$, $M_3$, $M_4$, $M_5$) and for anesthetizing a subject include a bitopic muscarinic antagonist or agonist. A bitopic muscarinic antagonist named JB-D4 was discovered. Additional bitopic muscarinic antagonists discovered and described herein include BK-23, HD-42, HD153, HD-185, KH-5, JM-31 and JM-32. These bitopic ligands and their structural analogs, as well as bitopic muscarinic agonists, may be used as neuromuscular blocking agents (e.g., for use in compositions for anesthetizing a subject) and for the treatment of central nervous system disorders (e.g., Parkinson's disease, Schizophrenia, etc.), Overactive Bladder Syndrome, Chronic Obstructive Pulmonary Disease, asthma, and many other diseases associated with the activation or inhibition of $M_1$-$M_5$ acetylcholine receptors.

9 Claims, 6 Drawing Sheets

Compound B

Compound E

Compound H

Compound K

Compound C

Compound F

Compound I

Compound L

Compound D

Compound G

Compound J

Compound M

Related U.S. Application Data application No. 13/937,350, filed on Jul. 9, 2013, now Pat. No. 9,156,833.

(60) Provisional application No. 61/671,976, filed on Jul. 16, 2012.

(51) Int. Cl.
*A61K 31/4453* (2006.01)
*C07D 405/06* (2006.01)
*C07D 417/06* (2006.01)
*C07D 295/104* (2006.01)

(52) U.S. Cl.
CPC ....... *C07D 295/104* (2013.01); *C07D 405/06* (2013.01); *C07D 417/06* (2013.01)

Compound B

Compound E

Compound C

Compound F

Compound D

Compound G

Compound H

Compound K

Compound I

Compound L

Compound J

Compound M

BITOPIC MUSCARINIC AGONISTS AND ANTAGONISTS AND METHODS OF SYNTHESIS AND USE THEREOF

CROSS-REFERENCE TO RELATED APPLICATIONS

This application is a continuation-in-part application of U.S. application Ser. No. 14/628,760, filed Feb. 23, 2015, which is a continuation application of U.S. application Ser. No. 13/937,350, filed Jul. 9, 2013, which claims the benefit of and priority to U.S. Provisional Application Ser. No. 61/671,976, filed Jul. 16, 2012, all of which are hereby incorporated by reference in their entireties, for all purposes, herein.

FIELD OF THE INVENTION

The invention relates generally to the fields of chemistry, molecular biology, and medicine. More particularly, the invention relates to synthesis and use of bitopic muscarinic receptor agonists and antagonists.

BACKGROUND

G-protein-coupled receptors (GPCRs) represent a large protein family responsible for mediating extracellular to intracellular signaling. They are located in the plasma membrane of all cell types of various tissues and are involved in the control of numerous central and peripheral physiological responses, as well as being a major drug target in human disease. This family of receptors consists of muscarinic receptors designated as $M_1$-$M_5$. Each receptor is a single subunit membrane protein with seven α-helical transmembrane spanning domains, three extracellular and three intracellular loops which form a pocket for ligand binding. The gene family as a whole has approximately 26% overall amino acid identity. The third loop which selectively couples with G proteins is particularly variable, showing 2.7% identity between receptors compared with an average of 66% identity found in the conserved transmembrane domains. $M_2$ and $M_4$ receptors normally couple to the pertusiss-toxin sensitive $G_{i/o}$-proteins, whereas $M_1$, $M_3$ and $M_5$ receptors couple to $G_{q/11}$-proteins. Smooth muscle contraction, particularly of airway, ileum, iris and bladder, is mediated primarily by $M_3$ muscarinic receptors and to a much lesser extent by $M_2$ receptors. Exocrine secretion, particularly of saliva and insulin, is primarily mediated by $M_3$ receptors and to a smaller extent by $M_1$ receptors. $M_2$ receptors in the heart have a profound role in the control of cardiac myocyte contraction. $M_1$ receptors have been found to play an important role in memory and learning while $M_4$ receptors are thought to mediate an inhibitory effect on striatal dopamine-mediated locomotor activity. Additionally, $M_2$ receptors located in the hypothalamus are likely to be involved in the regulation of body temperature whereas $M_3$ receptors have been reported to modulate appetite. These muscarinic receptor subtypes thus provide effective therapeutic targets for a number of neurological and psychiatric diseases such as Alzheimer's (AD), Schizophrenia and Parkinson's Disease (PD). Research has focused on the development of selective $M_1/M_5$ muscarinic agonists and $M_2$ antagonists as potential therapeutic targets for the symptomatic treatment of AD, $M_1/M_4$ agonists for Schizophrenia, and $M_1/M_4$ antagonists for Parkinson's Disease. In addition to central nervous system (CNS) disorders, selective $M_2$ and $M_3$ muscarinic antagonists can be beneficial for the treatment of disorders such as chronic obstructive pulmonary disease (COPD), asthma and overactive bladder (OAB) syndrome.

Classical approaches to GPCR drug design have targeted the orthosteric receptor binding site and most drugs are known to interact with this endogenous ligand-binding pocket. Since the orthosteric site is usually conserved across GPCR subtypes, orthosteric ligands must overcome many limitations, such as decreased selectivity, efficacy, and undesirable side effects, thus making the development of subtype-specific agonists and antagonists very difficult. G-protein receptors also contain topographically distinct and less conserved allosteric binding sites that are targeted to attain drug selectivity. Novel drugs that modulate receptor function by targeting these allosteric sites alter the biological properties of the endogenous orthostheric ligand by either changing its affinity and/or efficacy. Allosteric compounds show higher subtype selectivity, have a safer pharmacological profile and often do not induce receptor desensitization. Allosteric modulators have therefore considerable therapeutic potential but their signaling properties are only beginning to be explored. Researchers have begun to explore the potential of linking orthosteric and allosteric pharmacophores to yield bitopic ligands. Bitopic ligands are single molecules with two different structural motifs chemically attached in a manner that allow simultaneous binding to both allosteric and orthosteric sites of the receptor. The goal is to combine high affinity, via orthosteric sites, with high selectivity, via allosteric sites. Bitopic ligands may lead to novel drugs with improved affinity and/or selectivity profiles, and muscarinic acetylcholine receptors (mAChRs).

SUMMARY

Described herein are compositions, methods and kits for treating a condition associated with modulation of a muscarinic receptor (e.g., one or more of $M_1$, $M_2$, $M_3$, $M_4$, $M_5$). A bitopic muscarinic antagonist, named JB-D4, was discovered. Additional bitopic muscarinic antagonists discovered and described herein include BK-23, HD-42, HD153, HD-185, KH-5, JM-31 and JM-32. These bitopic ligands and other structural analogs, as well as bitopic muscarinic agonists, described herein may be used as neuromuscular blocking agents (e.g., for use in compositions for anesthetizing a subject), for the treatment of CNS disorders (e.g., Parkinson's disease, Schizophrenia, etc.), OAB syndrome, COPD, asthma, and many other diseases associated with the activation or inhibition of $M_1$-$M_5$ acetylcholine receptors, while providing, due to their bitopic nature, increased selectivity and efficacy compared to currently available therapeutics.

Accordingly, described herein is a composition including a pharmaceutically acceptable carrier and a bitopic muscarinic antagonist or agonist having the formula:

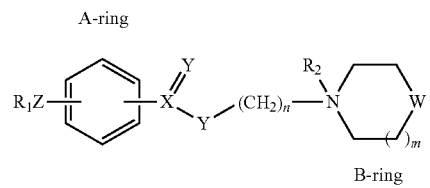

wherein:
$R_1$ is Me, Et, Pr, Bu, pentyl, or hexyl;
$R_2$ is H or Me;
X is C, O, or S;
Y is O, S or no group;
W is C, O, N, or S;
Z is C, O, or S;
n is 1-5 $CH_2$-group; and m= is 0 or 1; and wherein the B-ring can be a 5 (m=0) or 6 (m=1)-membered saturated or unsaturated ring containing one or more double bonds between any 2 carbon atoms and with W=C, O, N, or S at any position, or an analog or derivative thereof, in a therapeutically effective amount for activating or inhibiting activation of at least one muscarinic receptor (e.g., $M_1$, $M_2$, $M_3$, $M_4$ and $M_5$), in a subject. The composition can be formulated, for example, for oral or intravenous administration Also described herein is a composition including a pharmaceutically acceptable carrier and a bitopic muscarinic antagonist having the formula:

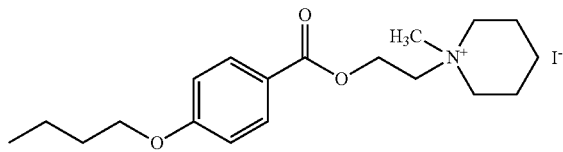 [SMILES: CCCCOc1ccc(C(=O)OCC[N+]2(C)CCCCC2)cc1 ; [I-]]

in a therapeutically effective amount for inhibiting activation of at least one muscarinic receptor (e.g., $M_1$, $M_2$, $M_3$, $M_4$ and $M_5$) in a subject. The composition can be formulated, for example, for oral or intravenous administration.

Further described herein is a kit for treating a disease or disorder associated with activity of a muscarinic receptor in a subject (e.g., human). A typical kit includes: a composition as described herein in a therapeutically effective amount for activating or inhibiting activity of at least one muscarinic receptor in the subject and alleviating or eliminating the disease or disorder in the subject; instructions for use; and packaging. The at least one muscarinic receptor can be one or more of, for example, $M_1$, $M_2$, $M_3$, $M_4$, and $M_5$. The disease or disorder can be, for example, a central nervous system disorder, overactive bladder syndrome, COPD, and asthma. The central nervous system disorder can be, for example, Parkinson's disease, Schizophrenia, drug addiction or AD. The composition can be formulated, for example, for oral or intravenous administration. In one embodiment of a kit, the bitopic muscarinic antagonist has the formula:

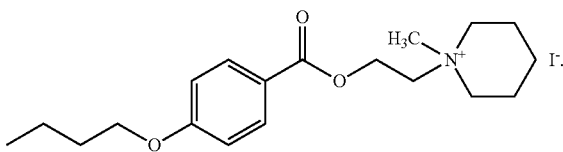

Also described herein is a method of treating a disease or disorder associated with activity of a muscarinic receptor in a subject. The method includes administering to the subject a composition as described herein in a therapeutically effective amount for activating or inhibiting activity of at least one muscarinic receptor in the subject and alleviating or eliminating the disease or disorder in the subject. The subject is typically a human, and the disease or disorder can be, for example, a central nervous system disorder, overactive bladder syndrome, COPD, or asthma. Examples of central nervous system disorders include Parkinson's disease, Schizophrenia, AD, and drug addiction. In the method, the composition can be administered, for example, orally or intravenously. Administration of the composition results in inhibition of activation of at least one muscarinic receptor, e.g., $M_1$, $M_2$, $M_3$, $M_4$, and $M_5$. In some embodiments, the bitopic muscarinic antagonist has the formula:

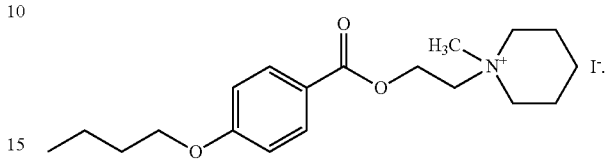

Yet further described herein is a method of anesthetizing a subject. The method includes administering to the subject a composition including a bitopic muscarinic antagonist having the formula:

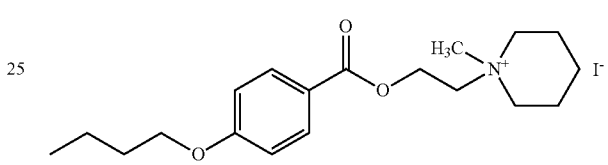

in an amount effective for inhibiting activation of $M_3$ and $M_4$ muscarinic receptors on smooth muscle tissues in the subject. The composition can further include an anesthesia agent. In one embodiment of the method, the composition is administered with a second composition including an anesthesia agent. In such an embodiment, the composition can be administered prior to, simultaneous to, or subsequent to administration of the second composition.

Also described herein is a composition including a pharmaceutically acceptable carrier and a bitopic muscarinic antagonist or agonist having the formula:

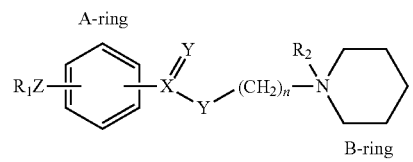

wherein:
$R_1$ is Me, Et, Pr, Bu, pentyl, or hexyl;
$R_2$ is H or Me;
X is C, O
Y is O or absent (Y couples A-ring to B-ring either by an ester or ether functionality)
Z is C, O, or S;
n is 1-5 $CH_2$-group; and wherein
the B-ring can saturated or unsaturated containing one or two double bonds between any 2 carbon atoms, or an analog or derivative thereof, in a therapeutically effective amount for activating or inhibiting activation of at least one muscarinic receptor (e.g., $M_1$, $M_2$, $M_3$, $M_4$ and $M_5$), in a subject.

In this embodiment, the composition can be formulated for oral or intravenous administration, for example. In one example of a composition, the bitopic muscarinic antagonist has the formula:

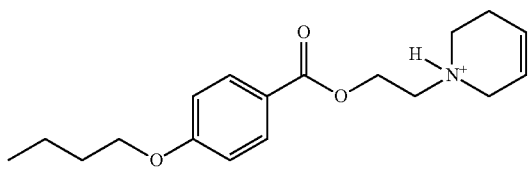

wherein:
R₁=Butyl,
R₂=H,
Z=O,
X=C,
Y=O,
n=2, in a therapeutically effective amount for inhibiting activation of at least one muscarinic receptor (e.g., M₁, M₂, M₃, M₄ and M₅) in a subject.

In another example of a composition, the bitopic muscarinic antagonist has the formula:

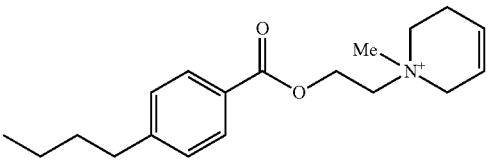

wherein:
R₁=Butyl,
R₂=Me,
Z=O,
X=C,
Y=O,
n=2, in a therapeutically effective amount for inhibiting activation of at least one muscarinic receptor (e.g., M₁, M₂, M₃, M₄ and M₅) in a subject.

In another example of a composition, the bitopic muscarinic antagonist has the formula:

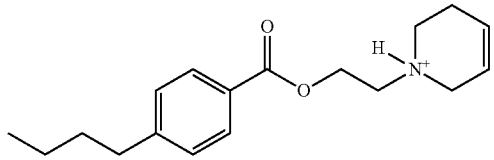

wherein:
R₁=Propyl,
R₂=H,
Z=CH₂,
X=C,
Y=O,
n=2, in a therapeutically effective amount for inhibiting activation of at least one muscarinic receptor (e.g., M₁, M₂, M₃, M₄ and M₅) in a subject.

In another example of a composition, the bitopic muscarinic antagonist has the formula:

wherein:
R₁=Propyl,
R₂=Me,
Z=CH₂,
X=C,
Y=O,
n=2, in a therapeutically effective amount for inhibiting activation of at least one muscarinic receptor (e.g., M₁, M₂, M₃, M₄ and M₅) in a subject.

In another example of a composition, the bitopic muscarinic antagonist has the formula:

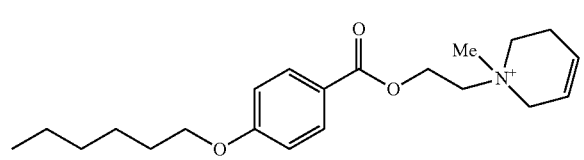

wherein:
R₁=Hexyl,
R₂=Me,
Z=O,
X=C,
Y=O,
n=2, in a therapeutically effective amount for inhibiting activation of at least one muscarinic receptor (e.g., M₁, M₂, M₃, M₄ and M₅) in a subject.

In another example of a composition, the bitopic muscarinic antagonist has the formula:

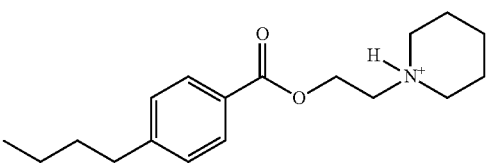

wherein:
R₁=Propyl,
R₂=H,
Z=CH₂,
X=C,
Y=O,
n=2, in a therapeutically effective amount for inhibiting activation of at least one muscarinic receptor (e.g., M₁, M₂, M₃, M₄ and M₅) in a subject.

In another example of a composition, the bitopic muscarinic antagonist has the formula:

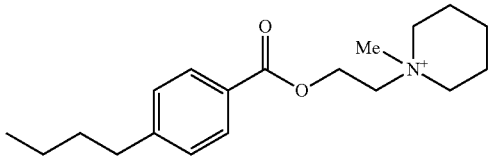

wherein:
$R_1$=Propyl,
$R_2$=Me,
Z=$CH_2$,
X=C,
Y=O,
n=2, in a therapeutically effective amount for inhibiting activation of at least one muscarinic receptor (e.g., $M_1$, $M_2$, $M_3$, $M_4$ and $M_5$) in a subject.

Also described herein is a kit for treating a disease or disorder associated with activity of a muscarinic receptor in a subject that includes a composition including a pharmaceutically acceptable carrier and a bitopic muscarinic antagonist or agonist having the formula:

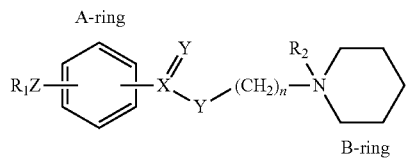

wherein:
$R_1$ is Me, Et, Pr, Bu, pentyl, or hexyl;
$R_2$ is H or Me;
X is C, O
Y is O or absent (Y couples A-ring to B-ring either by an ester or ether functionality)
Z is C, O, or S;
n is 1-5 $CH_2$-group; and wherein
the B-ring can saturated or unsaturated containing one or two double bonds between any 2 carbon atoms, or an analog or derivative thereof, in a therapeutically effective amount for activating or inhibiting activity of at least one muscarinic receptor ($M_1$, $M_2$, $M_3$, $M_4$, and $M_5$) in the subject and alleviating or eliminating the disease or disorder in the subject; instructions for use; and packaging. The disease or disorder can be, for example, a CNS disorder (e.g., PD, AD, Schizophrenia, drug addiction), overactive bladder syndrome, peptic ulcer, COPD, irritable bowel syndrome, overactive bladder syndrome, obesity, and asthma. The composition can be formulated for oral or intravenous administration, for example.

Still further described herein is a method of treating a disease or disorder associated with activity of a muscarinic receptor in a subject, the method including administering to the subject a composition including a pharmaceutically acceptable carrier and a bitopic muscarinic antagonist or agonist having the formula:

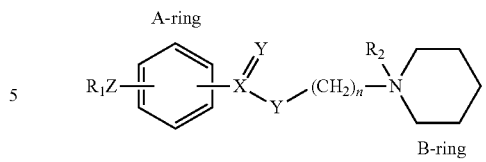

wherein:
$R_1$ is Me, Et, Pr, Bu, pentyl, or hexyl;
$R_2$ is H or Me;
X is C, O
Y is O or absent (Y couples A-ring to B-ring either by an ester or ether functionality)
Z is C, O, or S;
n is 1-5 $CH_2$-group; and wherein
the B-ring can saturated or unsaturated containing one or two double bonds between any 2 carbon atoms, or an analog or derivative thereof, in a therapeutically effective amount for activating or inhibiting activity of at least one muscarinic receptor in the subject and alleviating or eliminating the disease or disorder in the subject.

In the method, the subject is typically a human, and the disease or disorder can be, for example, a CNS disorder (e.g., PD, AD, Schizophrenia, drug addiction), overactive bladder syndrome, peptic ulcer, COPD, irritable bowel syndrome, overactive bladder syndrome, obesity, or asthma. The composition can be administered orally or intravenously, for example.

Yet further described herein is a method of anesthetizing a subject that includes administering to the subject a composition including a pharmaceutically acceptable carrier and a bitopic muscarinic antagonist or agonist having the formula:

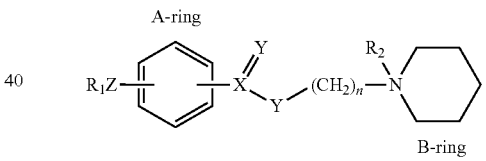

wherein:
$R_1$ is Me, Et, Pr, Bu, pentyl, or hexyl;
$R_2$ is H or Me;
X is C, O
Y is O or absent (Y couples A-ring to B-ring either by an ester or ether functionality)
Z is C, O, or S;
n is 1-5 $CH_2$-group; and wherein
the B-ring can saturated or unsaturated containing one or two double bonds between any 2 carbon atoms, or an analog or derivative thereof, in an amount effective for inhibiting activation of at least one muscarinic receptor (e.g., $M_2$, $M_3$ and $M_4$ muscarinic receptors) on smooth muscle tissues in the subject.

In this method, the composition can further include an anesthesia agent. The composition can be administered with a second composition including an anesthesia agent. In this embodiment, the composition can be administered prior to, simultaneous to, or subsequent to administration of the second composition.

Unless otherwise defined, all technical terms used herein have the same meaning as commonly understood by one of ordinary skill in the art to which this invention belongs.

The terms "patient," "subject" and "individual" are used interchangeably herein, and mean an invertebrate or vertebrate animal (e.g., mammal such as a human, rodent, non-human primate, canine, bovine, ovine, equine, feline, etc.) subject to be treated and/or to obtain a biological sample from. The compositions and methods described herein may find utility in both humans and animals, i.e., will have both medical and veterinary applications for treating a condition, disease or disorder associated with activity of one or more muscarinic receptors.

As used herein, "bind," "binds," or "interacts with" means that one molecule recognizes and adheres to a particular second molecule in a sample or organism, but does not substantially recognize or adhere to other structurally unrelated molecules in the sample. Generally, a first molecule that "specifically binds" a second molecule has a binding affinity greater than about $10^{-8}$ to $10^{-12}$ moles/liter for that second molecule and involves precise "hand-in-a-glove" docking interactions that can be covalent and noncovalent (hydrogen bonding, hydrophobic, ionic, and van der waals).

As used herein, the terms "regulating", "regulation", "modulating" or "modulation" refers to the ability of an agent to either inhibit or enhance or maintain activity and/or function of a molecule (e.g., a receptor). For example, an inhibitor of a muscarinic receptor would down-regulate, decrease, reduce, suppress, or inactivate at least partially the activity and/or function of the receptor. Up-regulation refers to a relative increase in function and/or activity.

By the term "JB-D4" is meant the compound described herein as "Compound A." This term encompasses the free base, a pharmaceutically acceptable salt or solvate thereof.

As used herein, the terms "BK-23", "HD-42", "HD153", "HD-185", "KH-5", "JM-31" and "JM-32" refer to the compounds shown in Tables 8 and 9. These terms encompass the free base, a pharmaceutically acceptable salt or solvate thereof for each compound. In Example 3 below, BK-23 is referred to as "9a," HD-42 is referred to as "10a," HD-153 is referred to as "9b," HD-185 is referred to as "10b," KH-5 is referred to as "10c," JM-31 is referred to as "14b" and JM-32 is referred to as "13b." The two names for each compound are used interchangeably herein.

As used herein, the term "bitopic" means binding to both allosteric and orthosteric receptor sites simultaneously.

By the phrase "bitopic muscarinic antagonist" is meant any agent (e.g., drug, compound, hormone, etc.) that forms a complex with or binds to receptors on a cell, thereby inhibiting the activity of such receptors.

By the phrase "bitopic muscarinic agonist" is meant any agent (e.g., drug, compound, hormone, etc.) that forms a complex with or binds to receptors on a cell, thereby initiating a physiological response.

The term "sample" is used herein in its broadest sense. A sample including polynucleotides, polypeptides, peptides, antibodies and the like may include a bodily fluid, a soluble fraction of a cell preparation or media in which cells were grown, genomic DNA, RNA or cDNA, a cell, a tissue, skin, hair and the like. Examples of samples include saliva, serum, blood, urine and plasma.

As used herein, the term "treatment" is defined as the application or administration of a therapeutic agent to a patient, or application or administration of the therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease, or the predisposition toward disease.

As used herein, the phrase "safe and effective amount" refers to the quantity of a component, which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a composition of the present invention effective to yield the desired therapeutic response. For example, an amount effective to prevent the occurrence of, delay the progression of, or mitigate the severity of AD, Schizophrenia drug addiction or withdrawal, etc. As another example, an amount effective for inhibiting activation or activity of $M_3$ and $M_4$ muscarinic receptors on neuromuscular cells for anesthetizing a subject. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or their derivatives.

Although compositions, kits, and methods similar or equivalent to those described herein can be used in the practice or testing of the present invention, suitable compositions, kits, and methods are described below. All publications, patent applications, and patents mentioned herein are incorporated by reference in their entirety. In the case of conflict, the present specification, including definitions, will control. The particular embodiments discussed below are illustrative only and not intended to be limiting.

DETAILED DESCRIPTION

Described herein are compositions, methods and kits for modulating muscarinic receptor activity and treating diseases and disorders associated with muscarinic receptor activity. A bitopic muscarinic antagonist of muscarinic $M_1$, $M_2$, $M_3$, $M_4$ and $M_5$ receptors was discovered and is referred to herein as JB-D4. Structural analogs of JB-D4, as well as bitopic muscarinic agonists and analogs thereof, are also described herein. Additional bitopic muscarinic antagonists discovered and described herein include BK-23, HD-42, HD153, HD-185, KH-5, JM-31 and JM-32. These bitopic ligands and other structural analogs can also be used for modulating muscarinic receptor activity and treating diseases and disorders associated with muscarinic receptor activity. Methods of synthesizing and using these compounds are described herein.

JB-D4, A Bitopic Muscarinic Receptor Antagonist and Analogs Thereof

A careful examination of the structural features of JB-D4 (also referred to herein as "Compound A"), reveals the classical NCCOC backbone of acetylcholine, the ammonium head-group, and a region of negative electrostatic potential. Not wishing to be bound by theory, the ammonium head group is believed to interact with the orthosteric site of muscarinic receptors while the p-butoxybenzoyl linker is believed to interact with the allosteric site in a bitopic manner. JB-D4 can be generated or synthesized using any suitable methods. An example of a method of synthesizing JB-D4 is described below in Example 2.

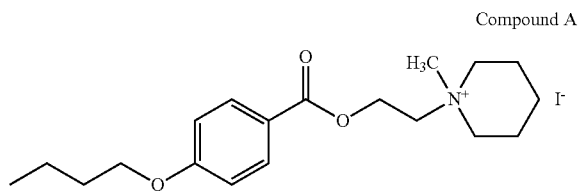 [SMILES: CCCCOc1ccc(C(=O)OCC[N+]2(C)CCCCC2)cc1 ; [I-]]

Compound A

JB-D4 has been shown to slow down dissociation of both the antagonist N-methyl scopolamine (NMS) and the agonist acetylcholine in kinetics experiments on cell lines stably transfected with $M_1$-$M_5$ muscarinic receptors. To probe the ability of JB-D4 to allosterically modulate orthosteric ligand, its effect on the rate of orthosteric radioligand dissociation has been investigated. In these experiments, a single concentration (0.1 mM and 1 mM) of JB-D4 has been tested for effects on the control [$^3$H] NMS and [$^3$H] acetylcholine dissociation rate at all $M_1$-$M_5$ mAChR, in full time course assays. The presence of JB-D4 has significantly slowed the dissociation rate of both [$^3$H] NMS and [$^3$H] acetylcholine from all $M_1$-$M_5$ receptors.

Figure 1A:
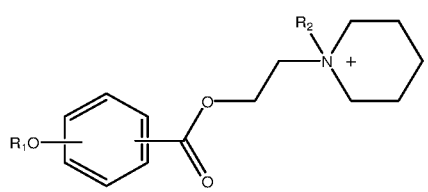
FIGS. 1A and 1B show structural analogs of JB-D4 expected to display similar muscarinic bitopic properties (Compounds B-M).
Figure 1A:
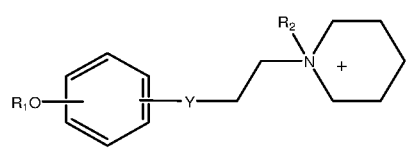
Figure 1A:
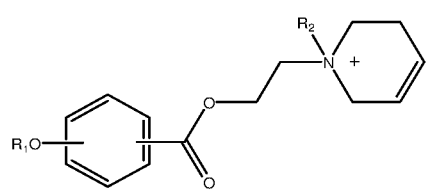
Figure 1A:
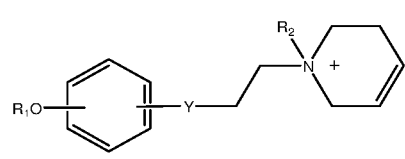
Figure 1A:
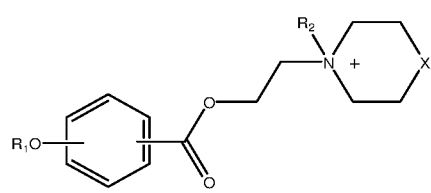
Figure 1A:
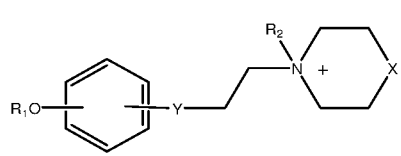
Figure 1B:
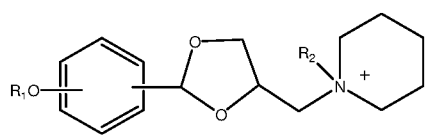
Figure 1B:
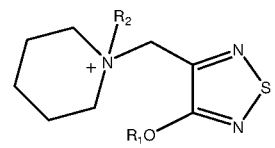
Figure 1B:
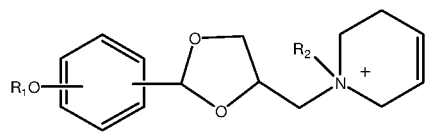
Figure 1B:
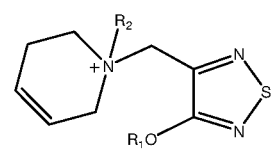
Figure 1B:
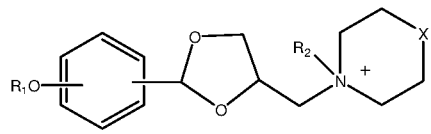
Figure 1B:
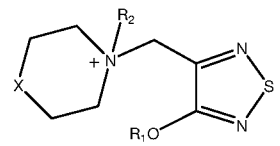
Figure 2:
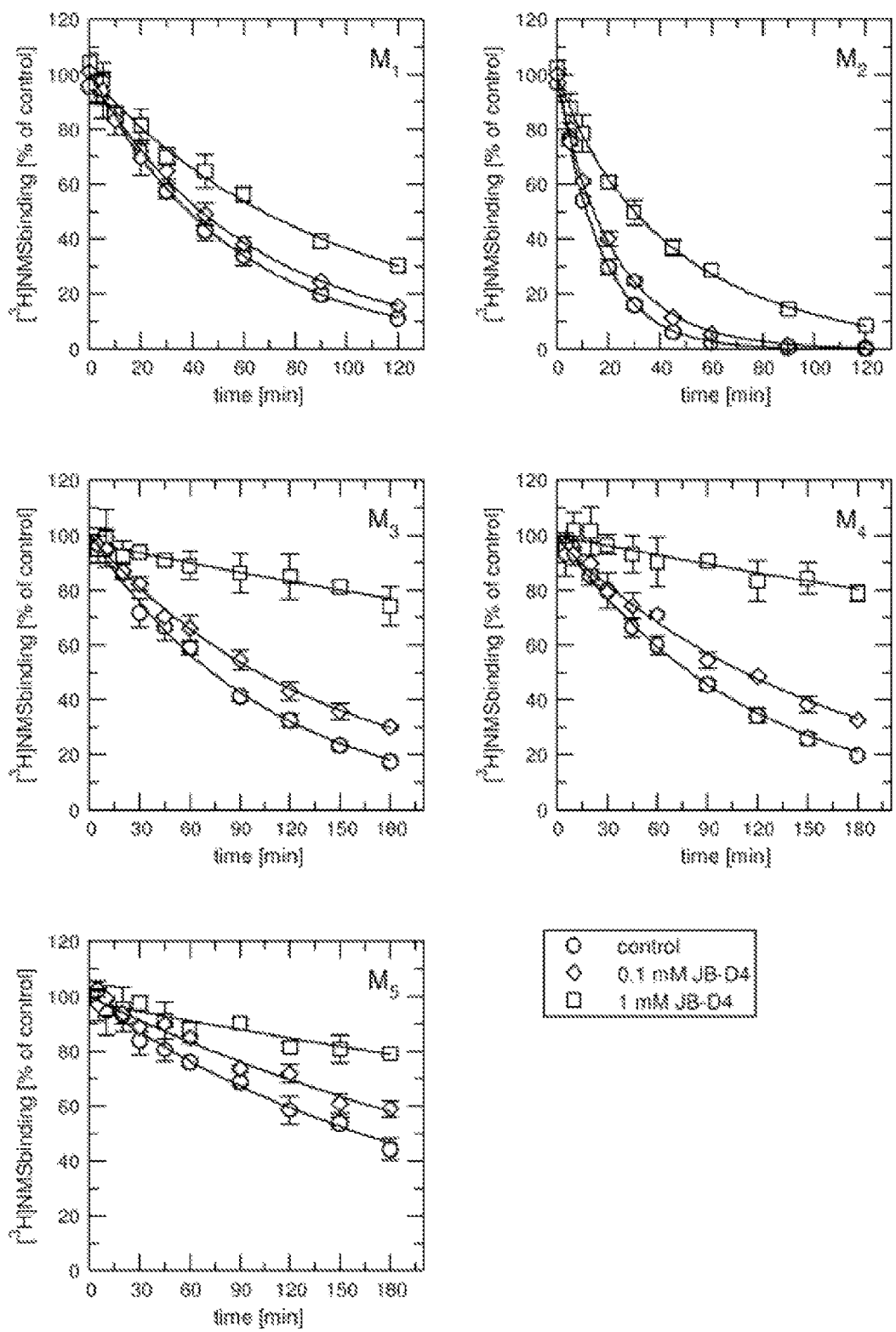
FIG. 2 is a series of graphs showing dissociation of [$^3$H] NMS.

JB-D4 has been shown to slow down dissociation of NMS to the extent comparable with classical allosteric modulators like gallamine and alcuronium (Table 1, FIG. 2). These two modulators are neuromuscular blocking agents indicated as adjuncts to general anesthesia. The presence of JB-D4 (1 mM) has significantly slowed the dissociation rate of [$^3$H] NMS from $M_1$ and $M_2$ receptors, $K_{off}$ [hr$^{-1}$] 0.61±0.06 (control 1.10±0.06) and 1.19±0.03 (3.7±0.2) respectively, whereas JB-D4 substantially and significantly reduced dissociation rate from $M_3$, $M_4$ and $M_5$ receptors, $K_{off}$ [hr$^{-1}$] 0.085±0.008 (control 0.57±0.03), 0.076±0.006 (control 0.54±0.020) and 0.083±0.005 (control 0.26±0.01), respectively.

TABLE 1

| | Dissociation of [$^3$H] NMS | | | | | | |
|---|---|---|---|---|---|---|---|
| | control | +0.1 mM JB-D4 | | | +1 mM JB-D4 | | |
| | $k_{off}$ [h$^{-1}$] | $k_{off1}$ [h$^{-1}$] | $f_2$ [%] | $k_{off2}$ [h$^{-1}$] | $k_{off1}$ [h$^{-1}$] | $f_2$ [%] | $k_{off2}$ [h$^{-1}$] |
| $M_1$ | 1.10 ± 0.06 | 0.91 ± 0.05 | 12 ± 1 | 1.15 ± 0.06 | 0.61 ± 0.06 | | |
| $M_2$ | 3.7 ± 0.2 | 2.8 ± 0.3 | 23 ± 2 | 3.2 ± 0.2 | 1.19 ± 0.03 | 12 ± 2 | 3.0 ± 0.4 |
| $M_3$ | 0.57 ± 0.03 | 0.41 ± 0.03 | | | 0.085 ± 0.008 | | |
| $M_4$ | 0.54 ± 0.02 | 0.38 ± 0.03 | | | 0.076 ± 0.006 | | |
| $M_5$ | 0.26 ± 0.01 | 0.18 ± 0.01 | | | 0.83 ± 0.005 | | |

Eq. 1 was fitted to the data from kinetic experiments. Data are means±SD from 3 independent experiments performed in quadruplicates. Equations:

$$y=(100-f_2)*e^{(-Koff1*X)}+f_2*e^{(-Koff2*X)} \quad \text{(Eq. 1)}$$

where y is the percentage of radioligand binding at time x of radioligand binding at time 0, $k_{off1}$ and $k_{off2}$ are rate dissociation constants and $f_2$ is the percentage of sites with $k_{off2}$ rate of dissociation.

$$y=f*e^{(-Koff*X)} \quad \text{(Eq. 2)}$$

where y is the percentage of radioligand binding at time x of radioligand binding at time 0, $k_{off}$ is rate dissociation constant and f is percentage of sites with $k_{off}$ rate of dissociation.

Figure 3:
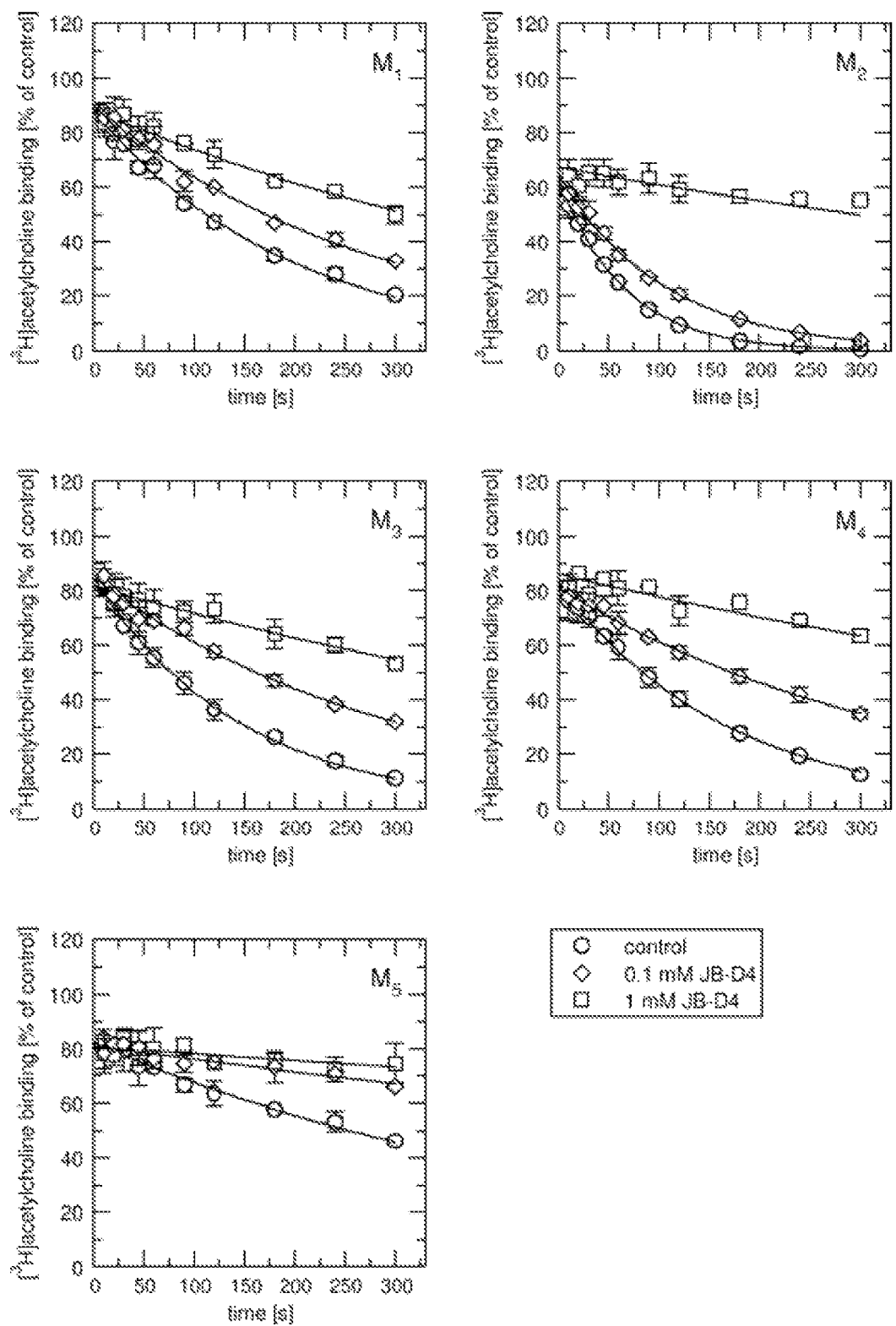
FIG. 3 is a series of graphs showing dissociation of [$^3$H] acetylcholine.

JB-D4 has been shown to slow down dissociation of acetylcholine dissociation stronger than those of gallamine and alcuronium (Table 2, FIG. 3). The presence of JB-D4 (1 mM) has significantly slowed the dissociation rate of [$^3$H] acetylcholine from $M_1$ receptors, $K_{off}$ [min$^{-1}$] 0.11±0.02 (control 0.30±0.02), whereas JB-D4 substantially and significantly reduced dissociation rate from $M_2$, $M_3$, $M_4$ and $M_5$ receptors, $K_{off}$ [min$^{-1}$] 0.039±0.005 (control 0.97±0.06), 0.084±0.007 (control 0.40±0.03), 0.049±0.005 (control 0.38±0.02), 0.033±0.005 (control 0.11±0.01), respectively.

TABLE 2

Dissociation of [3H] Acetylcholine

| | control | | +0.1 mM JB-D4 | | +1 mM JB-D4 | |
| --- | --- | --- | --- | --- | --- | --- |
| | f [%] | $k_{off}$ [min$^{-1}$] | f [%] | $k_{off}$ [min$^{-1}$] | f [%] | $k_{off}$ [min$^{-1}$] |
| $M_1$ | 89 ± 3 | 0.30 ± 0.02 | 90 ± 3 | 0.19 ± 0.02 | 88 ± 3 | 0.11 ± 0.02 |
| $M_2$ | 63 ± 3 | 0.97 ± 0.06 | 64 ± 4 | 0.56 ± 0.04 | 67 ± 3 | 0.039 ± 0.005 |
| $M_3$ | 85 ± 3 | 0.40 ± 0.03 | 84 ± 3 | 0.19 ± 0.02 | 82 ± 3 | 0.084 ± 0.007 |
| $M_4$ | 83 ± 3 | 0.38 ± 0.02 | 81 ± 4 | 0.18 ± 0.02 | 86 ± 3 | 0.049 ± 0.005 |
| $M_5$ | 82 ± 3 | 0.11 ± 0.01 | 81 ± 3 | 0.038 ± 0.05 | 81 ± 3 | 0.033 ± 0.005 |

Eq. 2 was fitted to the data from kinetic experiments. Data are means±SD from 3 independent experiments performed in quadruplicates.

Figure 4:
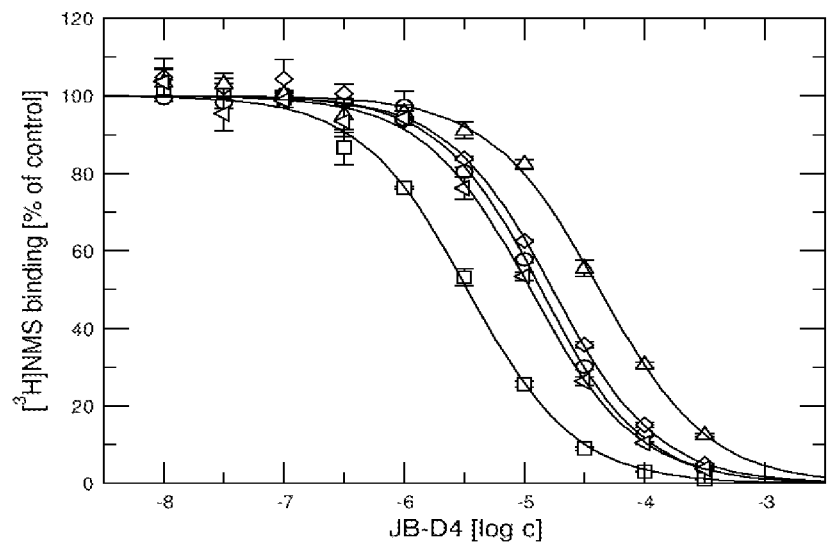
FIG. 4 is a graph showing an NMS binding assay concentration-response curve.

JB-D4 has been shown to fully inhibit both QNB and NMS binding, in competition experiments (FIG. 4), at all $M_1$-$M_5$ muscarinic receptors, demonstrating the competitive nature of JB-D4 at orthosteric muscarinic binding sites. Order of potencies determined from IC$_{50}$ values: $M_2$>$M_5$=$M_1$>$M_3$>$M_4$ in competition with NMS and $M_5$>$M_1$>$M_2$>$M_4$>$M_3$ in competition with the antagonist QNB (Table 3). JB-D4 affects binding of muscarinic orthosteric ligands (agonist acetylcholine and antagonist NMS) in a competitive as well as allosteric manner. JB-D4 thus is a bitopic ligand.

TABLE 3

Inhibition of NMS and QNB Binding

Competition with [$^3$H]NMS

| rec | IC$_{50}$_1 [μM] | IC$_{50}$_2 [μM] | IC$_{50}$_3 [μM] | avg IC$_{50}$ [μM] | SD | $K_D$ NMS [nM] | $K_I$ [μM] |
| --- | --- | --- | --- | --- | --- | --- | --- |
| M1 | 14.3 | 13.8 | 15.1 | 14.4 | 0.65574385 | 0.25 | 2.88 |
| M2 | 3.31 | 3.37 | 3.45 | 3.37666667 | 0.07023769 | 0.37 | 0.91194647 |
| M3 | 16.6 | 17.2 | 16.9 | 16.9 | 0.3 | 0.23 | 3.1601626 |
| M4 | 43.4 | 42 | 40 | 41.8 | 1.70880075 | 0.22 | 7.53770492 |
| M5 | 12.5 | 11.2 | 13.7 | 12.4666667 | 1.25033329 | 0.3 | 2.87692308 |

Competition with [$^3$H]QNB

| rec | IC$_{50}$_1 [μM] | IC$_{50}$_2 [μM] | IC$_{50}$_3 [μM] | avg IC$_{50}$ [μM] | SD | $K_D$ QNB [nM] | $K_I$ [μM] |
| --- | --- | --- | --- | --- | --- | --- | --- |
| M1 | 8.72 | 9.42 | 8.19 | 8.77666667 | 0.61695489 | 0.134 | 1.0371017 |
| M2 | 9.33 | 8.6 | 9.63 | 9.18666667 | 0.52974837 | 0.195 | 1.4990795 |
| M3 | 39.5 | 20.6 | 28.16 | 29.42 | 9.51279139 | 0.173 | 4.33901108 |
| M4 | 20.6 | 32.6 | 28.1 | 27.1 | 6.06217783 | 0.128 | 3.0751773 |
| M5 | 5.73 | 6.76 | 7.34 | 6.61 | 0.81541401 | 0.143 | 0.82697288 |

JB-D4 may be used as a neuromuscular blocker with potencies comparable or greater to gallamine and alcuronium due to its bitopic nature. The much weaker allosteric effects of gallamine and alcuronium on acetylcholine kinetics may be associated to the smaller molecular size of acetylcholine compared to the much larger antagonists NMS or QNB. Both gallamine and alcuronium may leave a slit at the binding site opening, small enough for small agonists like acetylcholine to slip through. This, however, was not observed for JB-D4. Thus, JB-D4 and analogs thereof may find use in anesthesiology applications, e.g., in compositions for anesthetizing a subject.

JB-D4 has the potential to be an effective modulator for the treatment of OAB syndrome due to the fact that it significantly slows down both acetylcholine and NMS dissociation at $M_3$ receptors (Tables 1 and 2). The efficacy of antimuscarinic ligands in the treatment of OAB syndrome is believed to arise through inhibition of bladder $M_3$, and to a lesser extent $M_2$, muscarinic receptors on detrusor smooth muscle cells, urothelium and bladder afferent nerves. Experimental research has shown that for treatment of OAB, slow dissociation of antagonists from the $M_3$ receptor is more important than selectivity based on affinity. Therefore, $M_3$ antagonists are desirable agents for the symptomatic treatment of OAB. JB-D4 (1 mM) substantially and significantly reduced the dissociation rate of both NMS and acetylcholine from $M_3$ receptors, $K_{off}$ (NMS) 0.085±0.008 (control 0.57±0.03) and $K_{off}$ (Acetylcholine) 0.084±0.007 (0.40±0.03).

JB-D4 has the potential to be an effective $M_5$ antagonist for the treatment of drug addiction and withdrawal due to the fact that it significantly slows down both acetylcholine and NMS dissociation at $M_5$ receptors (Tables 1, 2). JB-D4 (1 mM) substantially and significantly reduced the dissociation rate of both NMS and acetylcholine from $M_5$ receptors, $K_{off}$ (NMS) 0.083±0.005 (control 0.26±0.01) and $K_{off}$ (acetylcholine) 0.033±0.005 (0.11±0.03). The areas of the brain associated with rewarding properties of opiate-based analgesic drugs contain $M_5$ receptors expressed in dopamine containing neurons of the ventral tegmental area (VTA). Since the VTA plays a dominant role in the rewarding system of the brain, it has been hypothesized that $M_5$ antagonists could reduce the pleasurable effects associated with such drugs. Therefore, the discovery of $M_5$ antagonists could be of great therapeutic value in the treatment and prevention of substance abuse.

Analogs and derivatives of JB-D4 are encompassed by the present invention. Examples of structural analogs of JB-D4 that are expected to display muscarinic bitopic properties similar to JB-D4 are shown as Compounds B-M in FIG. 1. To generate a JB-D4 analog or derivative, JB-D4 can be modified according to Schematic 1 below, for example. The interaction between receptor sites (allosteric/orthosteric) and ligand is optimized by varying $R_1$ and value of n. Schematic 2 below shows a structure for an analog as described herein having a 5-membered B-ring.

Schematic 1

A-ring $R_1Z$—⬡—$X\overset{Y}{\underset{Y}{=}}$—$(CH_2)_n$—$N\overset{R_2}{\underset{()_m}{\diagdown W}}$ B-ring wherein:
$R_1$ is Me, Et, Pr, Bu, pentyl, or hexyl;
$R_2$ is H or Me;
X is C, O, or S;
  Y is O, S or no group;
W is C, O, N, or S
Z is C, O, or S;
  n is 1-5 $CH_2$-group; and
m= is 0 or 1; and wherein
the B-ring can be a 5 (m=0) or 6 (m=1)-membered saturated or unsaturated ring containing one or more double bonds between any 2 carbon atoms and with W=C, O, N, or S at any position.

Schematic 2

A-ring $R_1Z$—⬡—$X\overset{Y}{\underset{Y}{=}}$—$(CH_2)_n$—$N\overset{R_2}{\diagdown}$ B-ring Some examples of analogs are described herein (e.g., Compounds B-M of FIG. 1). Analogs can be generated or synthesized using any suitable methods. Examples of methods of synthesizing JB-D4 and analogs thereof are described below in Examples 1 and 2. With regard to synthesizing JB-D4 analogs or derivatives, JB-D4 can be modified by replacing the four-carbon alkoxy group ($R_1$) with one to six-carbon linkages at the two, three and four position of the benzene ring (Compound B) with n (# of $CH_2$) equal to two, m=1 and W=$CH_2$. The piperidinyl ring is also replaced by a tetrahydropyridine group (Compound C). The position of the double bond is situated between any 2 carbon atoms of the tetrahydropyridine moiety. Furthermore, 6-membered rings with X (N, O, S) at any position of B-ring in place of any carbon atom is incorporated as well (Compound D). In all compounds, $R_2$ can either be a hydrogen or methyl group. These analogs of the invention may display similar muscarinic bitopic biological properties.

A second series of compounds is synthesized and tested for muscarinic binding and functional activity. In this series of compounds, the ester functionality is replaced by an ether or thio-linkage (Y=S, O) to improve metabolic stability and functional selectivity, Compounds E-G. Esters can be hydrolyzed by choline acetylcholine esterase, the enzyme that breaks down acetylcholine at synaptic gaps after neurotransmission. In all compounds, $R_1$ are one- to six-carbon alkoxy substituents and $R_2$ can either be a hydrogen or methyl group. These structural analogs of the invention may display similar muscarinic bitopic biological properties.

A third series of compounds is synthesized in which the classical NCCOC backbone of acetylcholine is partly incorporated within a cyclic dioxolane moiety, Compounds H-J. Either oxygen atom of the 1,3-dioxolane moiety can serve as the region of negative electrostatic potential. These compounds are also expected to be more resistant to enzymatic hydrolysis. In all compounds, $R_1$ are one- to six-carbon alkoxy substituents and $R_2$ can either be a hydrogen or methyl group. These structural analogs of the invention may display similar muscarinic bitopic biological properties.

A fourth series of compounds is synthesized in which the 3-alkoxy-1,2,5-thiadiazo moiety is coupled with morpholine, piperidine and tetrahydropyridine, Compounds K-M. In all compounds, $R_1$ are one- to six-carbon alkoxy substituents and $R_2$ can either be a hydrogen or methyl group. These structural analogs of the invention may display similar muscarinic bitopic biological properties.

Compositions for Modulating Muscarinic Receptor(s) Activity

Compositions for modulating muscarinic receptors include a bitopic muscarinic receptor antagonist or agonist, or analog or derivative thereof, as described herein. Typically, the composition includes a pharmaceutically acceptable carrier and a bitopic muscarinic antagonist or agonist having the formula:

A-ring $R_1Z$—⬡—$X\overset{Y}{\underset{Y}{=}}$—$(CH_2)_n$—$N\overset{R_2}{\underset{()_m}{\diagdown W}}$ B-ring wherein:
$R_1$ is Me, Et, Pr, Bu, pentyl, or hexyl;
$R_2$ is H or Me;
X is C, O, or S;
  Y is O, S or no group;
W is C, O, N, or S;
Z is C, O, or S;
  n is 1-5 $CH_2$-group; and
m= is 0 or 1; and wherein
the B-ring can be a 5 (m=0) or 6 (m=1)-membered saturated or unsaturated ring containing one or more double bonds between any 2 carbon atoms and with W=C, O, N, or S at any position,
or an analog or derivative thereof. The bitopic muscarinic antagonist or agonist is in a therapeutically effective amount for activating or inhibiting activation of at least one muscarinic receptor (e.g., one or more of $M_1$, $M_2$, $M_3$, $M_4$ and $M_5$) in a subject. In a particular embodiment, the composition includes a pharmaceutically acceptable carrier and a bitopic muscarinic antagonist having the formula:

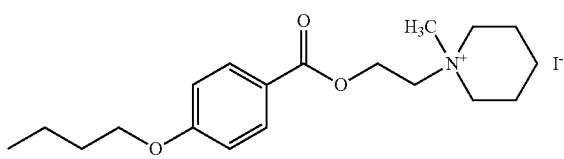

Compositions for use in anesthetizing a subject (e.g., a human in need thereof) will typically include a pharmaceutically acceptable carrier and a bitopic muscarinic antagonist that acts as a neuromuscular blocking agent. The bitopic muscarinic antagonist is in an amount effective to specifically activate $M_3$ and $M_4$ muscarinic receptors on smooth muscle tissues in the subject. An example of such a bitopic muscarinic antagonist is Compound A (JB-D4). However, suitable analogs or derivatives of Compound A may also be used.

The compositions described herein may be formulated for any suitable route of administration. Compositions may be administered orally, or parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation and may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that modulates activity of a muscarinic receptor(s), the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, and/or dispersing agents.

As indicated above, compositions (e.g., pharmaceutical compositions) described herein may be in a form suitable for sterile injection. To prepare such a composition, the suitable active therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Materials for use in the preparation of microspheres and/or microcapsules are, e.g., biodegradable/bioerodible polymers such as polygalactin, poly-(isobutyl cyanoacrylate), poly(2-hydroxyethyl-L-glutam-nine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly (glycolic acid) or poly(ortho esters) or combinations thereof). The bitopic muscarinic receptor agonists and antagonists described herein may be formulated as transdermal formulations, which may be administered using a variety of devices which have been described in the art (e.g., those described in U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, and 4,292,303 each of which is hereby incorporated by reference in its entirety).

Formulations for oral use include tablets containing the active ingredient(s) (e.g., a bitopic muscarinic receptor agonist or antagonist or a derivative thereof) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches such as potato starch, calcium carbonate, sodium chloride, lactose, calcium phosphate, calcium sulfate, or sodium phosphate); granulating and disintegrating agents (cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

Optionally, a composition as described herein may be administered in combination with any other appropriate therapy; such methods are known to the skilled artisan and described in Remington: The Science and Practice of Pharmacy, supra. Combinations are expected to be advantageously synergistic. Therapeutic combinations that specifically activate or specifically inhibit activation of one or more muscarinic receptors are identified as useful in the methods described herein.

Methods of Treating a Disease or Disorder Associated with Activity of a Muscarinic Receptor Described herein are methods of treating a disease or disorder associated with activity of a muscarinic receptor(s) in a subject. Typically the method includes administering to the subject a composition including a pharmaceutically acceptable carrier and a bitopic muscarinic antagonist or agonist having the formula:

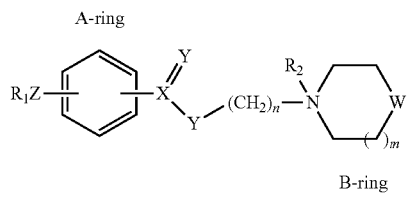

wherein:
$R_1$ is Me, Et, Pr, Bu, pentyl, or hexyl;
$R_2$ is H or Me;
X is C, O, or S;
  Y is O, S or no group;
W is C, O, N, or S;
Z is C, O, or S;
  n is 1-5 $CH_2$-group; and
m= is 0 or 1; and wherein
the B-ring can be a 5 (m=0) or 6 (m=1)-membered saturated or unsaturated ring containing one or more double bonds between any 2 carbon atoms and with W=C, O, N, or S at any position, or an analog or derivative thereof. The bitopic muscarinic antagonist or agonist is in a therapeutically effective amount for activating or inhibiting activity of at least one muscarinic receptor in the subject and alleviating or eliminating the disease or disorder in the subject. In a typical embodiment, the subject is a human and the disease or disorder is, for example, a CNS disorder (e.g., Parkinson's disease, Schizophrenia, AD, drug addiction and/or withdrawal), OAB syndrome, COPD, or asthma. The composition can be administered by any suitable route, e.g., orally or intravenously.

In one embodiment, in which the composition includes a bitopic muscarinic antagonist, administration of the composition results in inhibition of activation of at least one muscarinic receptor such as $M_1$, $M_2$, $M_3$, $M_4$, or $M_5$. In this embodiment, the bitopic muscarinic antagonist can be Compound A, for example. In one example, when used to treat drug addiction and withdrawal, the composition can include a bitopic muscarinic antagonist that specifically inhibits activation of $M_5$. In some embodiments, administration of the composition results in inhibition of activation of multiple muscarinic receptors (e.g., two or more of $M_1$, $M_2$, $M_3$, $M_4$, and $M_5$). For example, in anesthesiology applications, the bitopic muscarinic antagonist blocks activation of $M_3$ and $M_4$ muscarinic receptors. In another example, when used to treat OAB, the composition can include a bitopic muscarinic antagonist that specifically inhibits activation of $M_3$, and optionally, $M_2$.

In another embodiment, in which the composition includes a bitopic muscarinic agonist, administration of the composition results in activation of at least one muscarinic receptor such as $M_1$, $M_2$, $M_3$, $M_4$, or $M_5$. In this embodiment, the bitopic muscarinic agonist can be used for a number of neurological and psychiatric diseases including AD, Schizophrenia.

The therapeutic methods of the invention (which include prophylactic treatment) in general include administration of a therapeutically effective amount of a composition described herein to a subject in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, genetic marker, family history, and the like).

The administration of a composition including a bitopic muscarinic antagonist or agonist, or a derivative thereof, for the treatment of a disease or disorder associated with activity of a muscarinic receptor(s) may be by any suitable means that results in a concentration of the therapeutic that, (e.g., in some embodiments, when combined with other components), is effective in inhibiting or promoting, respectively, activation of the muscarinic receptor(s). The bitopic muscarinic antagonist or agonist, or derivative thereof, may be contained in any appropriate amount in any suitable carrier substance, and is generally present in an amount of 1-95% by weight of the total weight of the composition. As described above, the composition may be administered locally or systemically (e.g., parenteral, orally, subcutaneously, intravenously, intramuscularly, or intraperitoneally).

In one embodiment, the invention provides a method of monitoring treatment progress. The method includes the step of determining a level of change in one or more suitable parameters or markers depending upon the disease or disorder being treated, using, for example, one or more diagnostic markers or diagnostic measurement (e.g., screen, assay) in a subject suffering from or susceptible to a disorder or symptoms thereof associated with activity of one or more muscarinic receptors in which the subject has been administered a therapeutic amount of a composition as described herein. The level of marker determined in the method can be compared to known levels of marker in either healthy normal controls or in other afflicted patients to establish the subject's disease status. In preferred embodiments, a second level of marker in the subject is determined at a time point later than the determination of the first level, and the two levels are compared to monitor the course of disease or the efficacy of the therapy. In certain preferred embodiments, a pre-treatment level of marker in the subject is determined prior to beginning treatment according to the methods described herein; this pre-treatment level of marker can then be compared to the level of marker in the subject after the treatment commences, to determine the efficacy of the treatment.

Methods of Anesthetizing a Subject

As described above, JB-D4 has the potential to be a neuromuscular blocker with potencies comparable or greater to gallamine and alcuronium due to its bitopic nature. JB-D4 has been shown to slow down dissociation of NMS to the extent comparable with gallamine and alcuronium (Table 1, FIG. 2) which are neuromuscular blocking agents indicated as adjuncts to general anesthesia. Thus, JB-D4 may be used as an adjunct in anesthesiology procedures. A typical method of anesthetizing a subject includes administering to the subject a composition including a pharmaceutically acceptable carrier or excipient and a bitopic muscarinic antagonist having the formula:

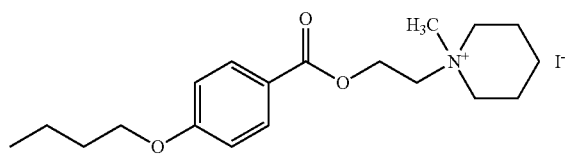 [SMILES: CCCCOc1ccc(C(=O)OCC[N+]2(C)CCCCC2)cc1 ; [I-]]

The bitopic muscarinic antagonist is in an amount (a concentration) effective for inhibiting activation of at least one muscarinic receptor on smooth muscle cells, e.g., $M_3$ and $M_4$ muscarinic receptors on smooth muscle tissues in the subject (e.g. a human in need of anesthesia). Such a composition can further include an anesthesia agent. Examples of anesthesia agents include gallamine and alcuronium. In another embodiment, the composition can be administered with a second composition that includes an anesthesia agent. In this embodiment, the composition can be administered prior to, simultaneous to, or subsequent to administration of the second composition.

In addition to JB-D4, other compounds can be used for anesthetizing a subject. In another example of a compound and method for anesthetizing a subject, the composition includes a pharmaceutically acceptable carrier and a bitopic muscarinic antagonist or agonist having the formula:

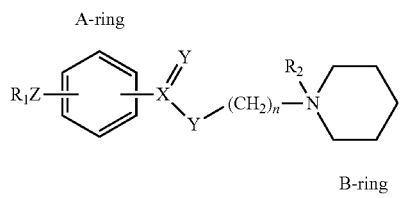

wherein:
$R_1$ is Me, Et, Pr, Bu, pentyl, or hexyl;
$R_2$ is H or Me;
X is C, O
Y is O or absent (Y couples A-ring to B-ring either by an ester or ether functionality)
Z is C, O, or S;
n is 1-5 $CH_2$-group; and wherein
the B-ring can saturated or unsaturated containing one or two double bonds between any 2 carbon atoms, or an analog or derivative thereof, in a therapeutically effective amount for activating or inhibiting activation of at least one muscarinic receptor selected from the group consisting of: $M_1$, $M_2$, $M_3$, $M_4$ and $M_5$, in a subject.

In this example, compounds with $R_2$=H and $R_2$=Me (e.g., $M_1$-$M_5$ antagonists) can be used for (as) local and general anesthesia. Such a compound is administered in an amount effective for inhibiting activation of at least one muscarinic receptor (e.g., one or more of $M_2$, $M_3$ and $M_4$ muscarinic receptors) on smooth muscle tissues in the subject. In a composition, two or more different muscarinic receptor antagonists can be included. Similarly, two compositions, each including one muscarinic receptor that is different from the other (e.g., one composition including an $M_2$ muscarinic receptor antagonist and a second composition including an $M_3$ muscarinic receptor antagonist), can be administered to a subject for local or general anesthesia. A composition including at least one muscarinic receptor antagonist as described herein can further include an anesthesia agent (i.e., an anesthesia agent that is not a muscarinic receptor antagonist). A composition including at least one muscarinic receptor antagonist as described herein can be administered with a second composition including an anesthesia agent (i.e., an anesthesia agent that is not a muscarinic receptor antagonist). In such a method, the composition can be administered prior to, simultaneous to, or subsequent to administration of the second composition.

Effective Doses

The compositions described herein are preferably administered to an animal (e.g., rodent, human, non-human primates, canine, bovine, ovine, equine, feline, etc.) in an effective amount, that is, an amount capable of producing a desirable result in a treated subject (e.g., inhibiting or promoting activation of a specific muscarinic receptor(s) in the subject, anesthetizing a subject, etc.). Toxicity and therapeutic efficacy of the compositions utilized in methods of the invention can be determined by standard pharmaceutical procedures. As is well known in the medical and veterinary arts, dosage for any one animal depends on many factors, including the subject's size, body surface area, body weight, age, the particular composition to be administered, time and route of administration, general health, the clinical symptoms of the disease or disorder and other drugs being administered concurrently (if any). A composition as described herein is typically administered at a dosage that sufficiently inhibits or promotes activation of a specific muscarinic receptor(s) for treating, alleviating or preventing the diseases and disorders described herein or for anesthetizing a subject. As an example, a typical dose of JB-D4 for modulating activity (e.g., activation) of at least one muscarinic receptor in a subject is in the range of about 0.1 mg/day to about 1000 mg/day for a mammal. Such a dose is typically administered daily. However, depending on the subject and the disease or disorder being treated (or the anesthesia regimen), a dose may be administered multiple times a day, hourly, weekly, as-needed, etc.

Kits for Treating a Disease or Disorder Associated with Activity of a Muscarinic Receptor(s) in a Subject and for Anesthetizing a Subject Described herein are kits for treating a disease or disorder associated with activity of a muscarinic receptor(s) in a subject and for anesthetizing a subject. A typical kit includes a composition including a therapeutically effective amount of a bitopic muscarinic antagonist or agonist, or a derivative thereof, for modulating activity (e.g., activation) of at least one muscarinic receptor in a subject, packaging, and instructions for use. In a kit, the composition may further include a pharmaceutically acceptable carrier in unit dosage form. If desired, a kit for anesthetizing a subject may also contain an effective amount of an additional anesthesia agent (e.g., gallamine, alcuronium, etc.). In some embodiments, the kit includes a sterile container which contains a therapeutic or prophylactic composition; such containers can be boxes, ampules, bottles, vials, tubes, bags, pouches, blister-packs, or other suitable container forms known in the art. Such

EXAMPLES

The present invention is further illustrated by the following specific examples. The examples are provided for illustration only and should not be construed as limiting the scope of the invention in any way.

Example 1

Synthesis of JB-D4 and Structural Analogs

Method 1—p-alkoxy ester N-substituted piperidine and morpholine salts (Compounds B, D): Compound 1 is formed from the reaction of 2-bromoethanol with piperidine or morpholine. Compound 2 is obtained from the reaction of 1 with p-alkoxy benzoyl chloride in anhydrous ether. The corresponding hydrochloride and methyl iodide salts are obtained by reacting 2 with either HCl gas or methyl iodide, respectively.

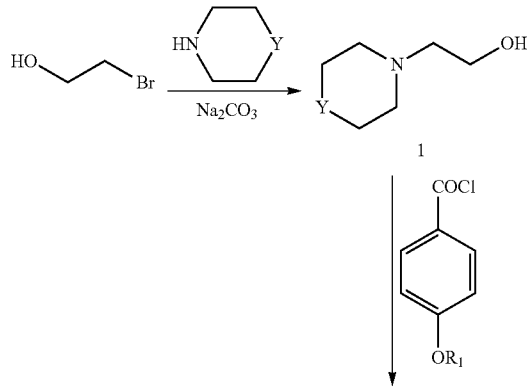

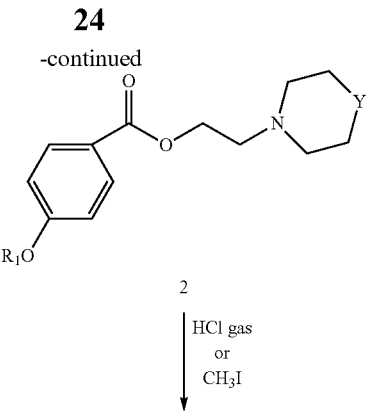

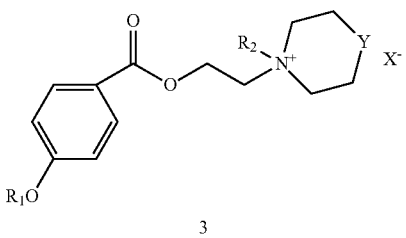

$R_2$ = H, Me
$R_1$ = Me, Et, Pr, butyl, pentyl, hexyl
X = Cl, I
Y = $CH_2$, O

Method 2—p-alkoxy ester N-substituted tetrahydro pyridine salts (Compound C): Compound 4 is formed from the reaction of 2-bromoethanol with pyridine. Compound 5 is obtained from the reduction of 4 with sodium borohydride. Reaction of 5 with p-alkoxy benzoyl chlorides in anhydrous ether yields compounds 6. The corresponding hydrochloride and methyl iodide salts 7 are obtained by reacting 6 with either HCl gas or methyl iodide, respectively.

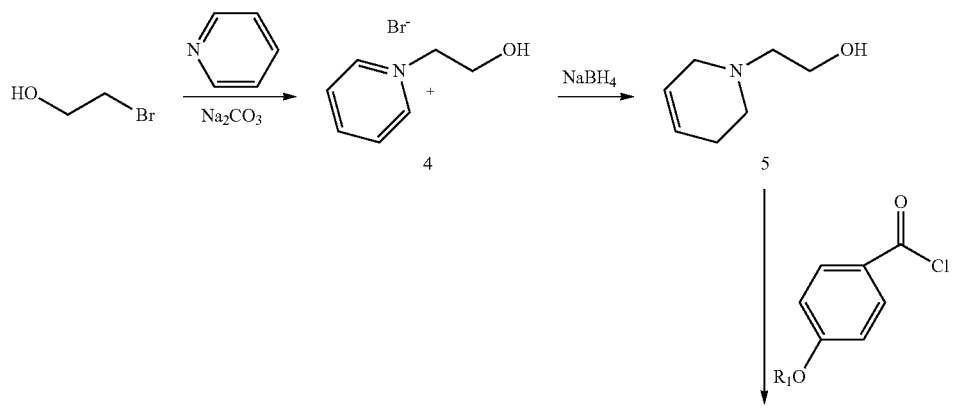

25 26

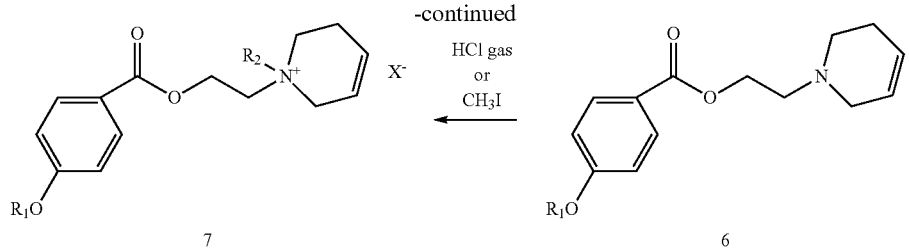

R₂ = H, Me
R₁ = Me, Et, Pr, butyl, pentyl, hexyl
X = Cl, I

Method 3—p-alkoxy ether and thioether N-substituted piperidine and morpholine salts (Compounds E, G): Reaction of morpholine or piperidine with 2-bromoethanol affords compounds 8. Reaction of compounds 8 with mesyl-chloride produces compounds 9. Reaction of compounds 9 with either p-alkoxyphenoxide or thio salts yields compounds 10. Reaction of compounds 10 with HCl or methyl iodide produces salts 11.

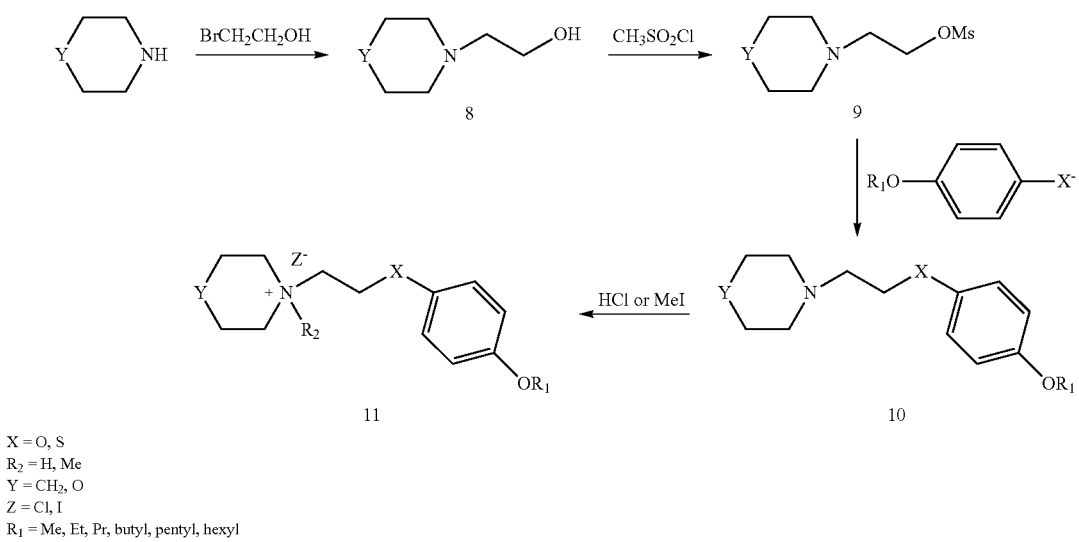

X = O, S
R₂ = H, Me
Y = CH₂, O
Z = Cl, I
R₁ = Me, Et, Pr, butyl, pentyl, hexyl

Method 4—p-alkoxy ether and thio ether N-substituted tetrahydro pyridine salts (Compound F): Reaction of pyridine with 2-bromoethanol affords compound 12. Reaction of compound 12 with sodium borohydride followed by mesyl-chloride produces compound 13. Reaction of compound 13 with either p-alkoxyphenoxide or thio salts yields compounds 14. Reaction of compounds 14 with HCl or MeI produce salts 15.

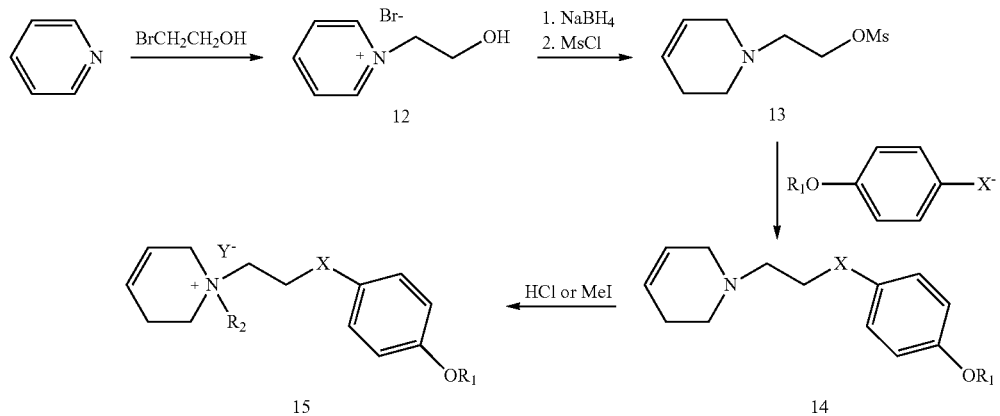

X = O, S
Y = Cl, I
$R_2$ = H, Me
$R_1$ = Me, Et, Pr, butyl, pentyl, hexyl

Method 5—p-alkoxy-1,3-dioxoxolane N-substituted piperidine and tetrahydro pyridine (Compounds H, I): Reaction of p-alkoxy benzaldehyde and 3-bromo-1,2-ethanediol can afford compound 16. Reaction of 16 with piperidine, followed by HCl gas or iodomethane can yield salts 17. Reaction of 16 with pyridine, followed by reduction with NaBH₄ and then HCl or iodomethane can produce salts 18.

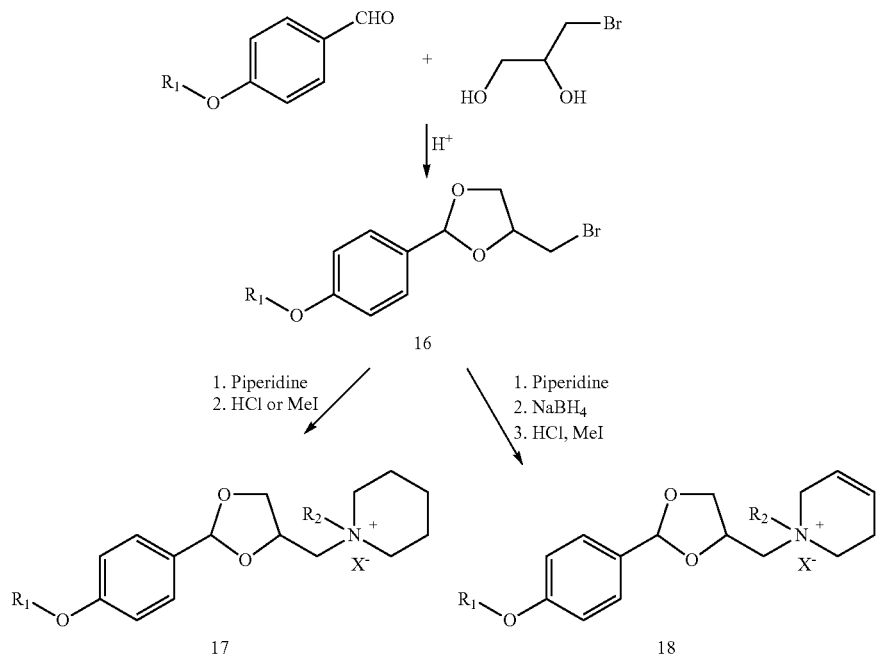

$R_2$ = H, Me
$R_1$ = Me, Et, Pr, butyl, pentyl, hexyl
X = Cl, I

Method 6—3-alkoxy-1,2,5-thiadiazo N-substituted tetrahydropyridine salts (Compound L): Oxidation of alcohol 5, followed by condensation with ammonium ion produces compound 20. Reaction of 20 with S₂Cl₂ provides compound 21. Reaction of 21 with an alcohol in the presence of sodium metal affords compound 22. Reaction of 22 with iodomethane or hydrogen chloride produces compounds 23.

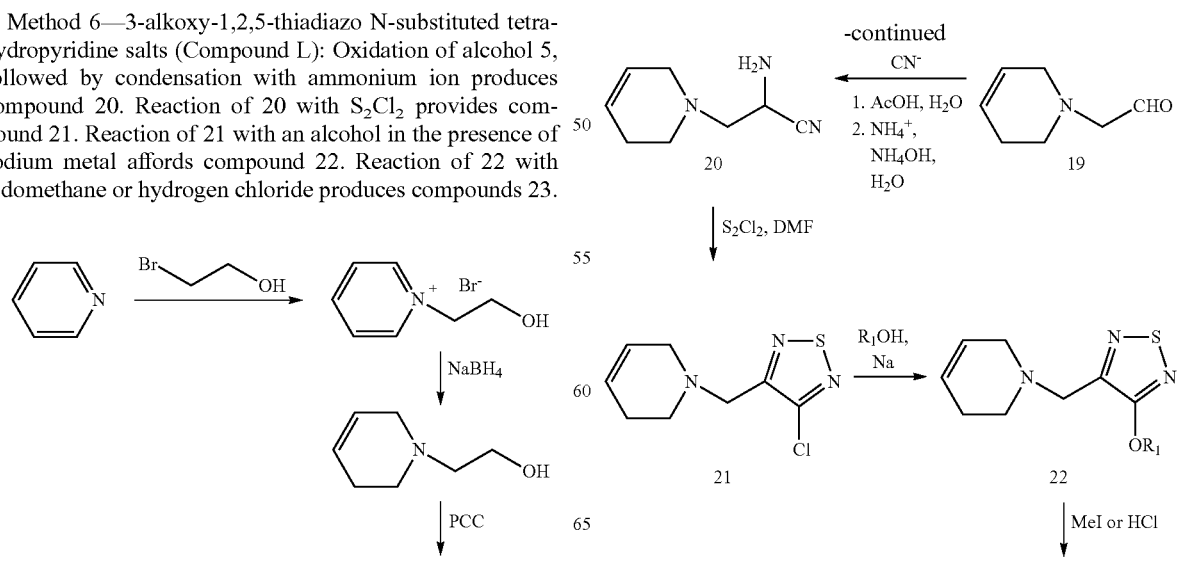

-continued

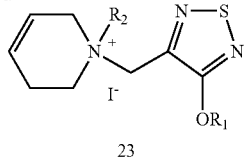

23

R$_2$ = H, Me
R$_1$ = Me, Et, Pr, butyl, pentyl, hexyl

Example 2

Synthesis of JB-D4

Route 1:
[2-Bromoethyl p-butoxybenzoate] To a 100-mL round bottom flask were added 2-bromoethanol (0.625 g, 0.005 mol), triethylamine (0.505 g, 0.005 mol) and 5 mL of dry anhydrous ether. The flask was cooled in an ice-bath and p-butoxybenzoylchloride (1.06 g, 0.005 mol) was added dropwise. The mixture was then refluxed for 30 minutes. The solution was filtered and 15 mL of 1 M HCl was added to the filtrate. The mixture was extracted several times with water. The ether layer was dried over anhydrous magnesium sulfate, filtered and concentrated under vacuum to yield compound 1 (0.41 g, 27%). $^1$H NMR (300 MHz, CDCl$_3$) δ 8.0 (2H), 7.0 (2H), 4.6 (2H), 4.2 (2H), 3.6 (2H), 1.8 (2H), 1.6 (2H), 1.0 (3H). MS: m/z 300 (M$^+$), 121, 138 (base peak).

[2-(N-piperidine ethyl) p-butoxybenzoate]. Compound 1 (0.41 g, 0.00113 mol), 20 mL of acetonitrile, 1.0 g sodium carbonate and piperidine (0.116 g, 0.00113 mol) were added to a 100-mL boiling flask and left to stir overnight. The solution was filtered and concentrated under vacuum to yield 0.39 g of crude compound 2. The crude material was chromatographed over silica with a 10:1 mixture of CH$_2$Cl$_2$/MeOH to give compound 2 (0.36 g, 88%). $^1$H NMR (300 MHz, CD$_3$COCD$_3$) δ 8.0 (2H), 7.1 (2H), 4.5 (2H), 4.2 (2H), 2.8 (2H), 2.6 (4H), 1.8 (2H), 1.6 (4H), 1.5 (2H), 1.0 (5H). MS: m/z 305 (M$^+$), 165, 98, 138 (base peak).

[2-(N-piperidine ethyl) p-butoxy benzoylester N-methyl Iodide] (JB-D4) Compound 2 (0.36 g, 0.00118 mol) and 1 mL of iodomethane were added to a 25 mL boiling flask and stirred overnight. The mixture was concentrated to yield crude salt 3 (0.50 g, 63%). The salt was recrystallized from n-butanol, m.p. 111-113° C. $^1$H NMR (300 MHz, D$_2$O) δ 7.9 (2H), 7.0 (2H), 4.6 (2H), 4.1 (2H), 3.8 (2H), 3.5-3.3 (4H), 3.1 (3H), 1.9-1.8 (4H), 1.7-1.5 (4H), 1.45-1.35 (2H), 0.9-0.8 (3H). Anal. Calcd. For C$_{19}$H$_{30}$NO$_3$I: C, 51.03%; H, 6.71%; N, 3.13%; I, 28.38%. Found: C, 50.48%; H, 6.59%; N, 3.19%; I, 30.29%.

Route 2:
[N-(2-hydroxyethyl)piperidine] 2-bromoethanol (1.40 g, 0.0112 mol), sodium carbonate (2.00 g, 0.019 mol) and 15 ml of acetonitrile were transferred to a 100 ml boiling flask. A mixture of piperidine (0.952 g, 0.0112 mol) in 5 mL of acetonitrile was added dropwise to the bromoethanol solution and stirred for two days at room temperature. The reaction mixture was filtered, concentrated and washed several times with anhydrous ether. The ether extracts were combined and concentrated to afford 0.53 gram of compound 1, a colorless liquid (36.8%). $^1$H NMR (300 MHz, CDCl$_3$) δ 1.4-1.5 (2H), 1.5-1.65 (4H), 2.35-2.45 (4H), 2.45-2.5 (t, 2H), 3.25-3.35 (bs, 1H), 3.55-3.6 (t, 2H).

[2-(N-piperidine ethyl) p-butoxybenzoate hydrochloride] N-(2-hydroxyethyl)piperidine (1.05 g, 0.00815 mol), p-butoxybenzoyl chloride (1.7 g, 0.0080 mol) and 50 mL of anhydrous ether were added to a 100 mL boiling flask and stirred to form a white precipitate within minutes. The reaction mixture was concentrated and precipitate washed several times with anhydrous ether to afford 0.77 grams of compound 2 (28.2%). $^1$H NMR (300 MHz, D$_2$O) δ7.9 (2H), 6.9 (2H), 4.5 (2H), 4.0 (2H), 3.8 (2H), 3.6-3.2 (4H), 1.9-1.8 (4H), 1.7-1.5 (4H), 1.45-1.35 (2H), 0.9-0.8 (3H).

[2-(N-piperidine ethyl) p-butoxybenzoate] Compound 2 (0.77 g, 0.00226 mol) was neutralized with saturated aqueous sodium carbonate. The solution was extracted with ether and combined extracts was dried over anhydrous magnesium sulfate. The solution was filtered, filtrate was concentrated to afford 0.40 gram of compound 3 (58.8%). $^1$H NMR (300 MHz, CD$_3$COCD$_3$) δ 8.0 (2H), 7.1 (2H), 4.5 (2H), 4.2 (2H), 2.8 (2H), 2.6 (4H), 1.8 (2H), 1.6 (4H), 1.5 (2H), 1.0 (5H). MS: m/z 305 (M$^+$), 165, 98, 138 (base peak).

[2-(N-piperidine ethyl) p-butoxybenzoate N-methyl iodide] (JB-D4) Compound 3 (0.40 g, 0.00131 mol) was dissolved in 6 ml of HPLC-grade acetone and excess methyl iodide was added and the mixture stirred for four hours at room temperature. The reaction mixture was concentrated to afford 0.55 gram of compound 4 (94%), m.p. 108-110° C. Compound 4 was recrystallized from t-butyl alcohol to yield 0.311 gram (56.5%) of a white powder, m.p. 124-125° C. $^1$H NMR (300 MHz, D$_2$O) δ 7.9 (2H), 7.0 (2H), 4.6 (2H), 4.1 (2H), 3.8 (2H), 3.5-3.3 (4H), 3.1 (3H), 1.9-1.8 (4H), 1.7-1.5 (4H), 1.45-1.35 (2H), 0.9-0.8 (3H). Anal. Calcd. For C$_{19}$H$_{30}$NO$_3$I: C, 51.03%; H, 6.71%; N, 3.13%; I, 28.38%. Found: C, 50.48%; H, 6.59%; N, 3.19%; I, 30.29%.

Example 3

Probing the Muscarinic Pharmacophore with Novel and Functionally Selective Non-Competitive Antagonists In this Example, BK-23 is referred to as "9a," HD-42 is referred to as "10a," HD-153 is referred to as "9b," HD-185 is referred to as "10b," KH-5 is referred to as "10c," JM-31 is referred to as "14b" and JM-32 is referred to as "13b."

Novel muscarinic antagonists were synthesized and used as chemical probes in structure-activity relationship (SAR) studies to obtain additional information of the muscarinic pharmacophore. The design of these ligands made use of current orthosteric and allosteric models of drug-receptor interactions together with chemical motifs known to achieve muscarinic receptor selectivity. This approach has led to the discovery of several bitopic muscarinic ligands that strongly bind at a secondary receptor site. In particular, compounds 9b and 10a-b were found to be non-competitive M$_1$/M$_4$ functionally selective antagonists that completely abolished carbachol activation in functional assays. Furthermore, these compounds appeared to be selective dual-steric non-competitive inverse partial agonists as they decreased basal receptor activity.

We have synthesized muscarinic ligands that were found to be functionally selective non-competitive antagonists 4. They all contain a para-disubstituted alkyl or alkoxy (R$_1$) phenyl group linked to a tetrahydropyridinyl ring. The positively charged tetrahydropyridinyl group most likely interacts with the orthosteric receptor site whereas the hydrophobic phenyl moiety interacts more strongly with the secondary receptor site.

(4)

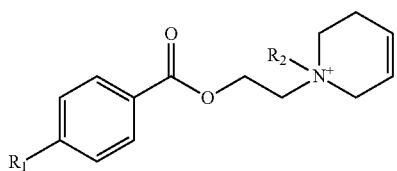

(5)

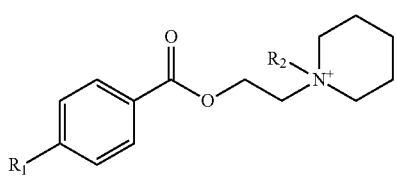

Several compounds 9b and 10a-b (Scheme 1) were found to be non-competitive $M_1/M_4$ functionally selective antagonists. Other compounds 5 of similar structural features, with a substituted piperidinyl ring, were also synthesized and found to exhibit similar biological profiles. The bitopic antagonist 13a (Scheme 2), our lead compound which led to the synthesis of all other analogs was found to slow down the dissociation of both N-methyl scopolamine (NMS) and acetylcholine to the extent comparable to classical allosteric modulators gallamine and alcuronium at $M_1$-$M_5$ muscarinic receptors (Boulos, J. et al., *J. Heter. Chem.* 2013, 50, 6, 1363-1367).

Muscarinic acetylcholine receptor subtypes play important roles at various levels of the basal ganglia motor circuit. $M_1$ receptors participate in the overall regulation of basal ganglia function and antiparkinsonian effects of muscarinic antagonists (Xiang, Z. et al., *J. Pharmacol. Exp. Ther.* 2012, 340, 3, 595-603). The competitive orthosteric $M_1$ selective antagonist VU0255035 was found to inhibit induction of generalized seizures by the agonist pilocarpine without the cognitive impairing effects of the antagonist scopolamine in a behavioral measure of hippocampus-dependent learning (Sheffler, D. et al., *Mol. Pharmacol.* 2009, 76, 356-368). $M_4$ muscarinic receptors, widely expressed in different regions of the forebrain and co-expressed with D1 dopamine receptors in a specific subset of striatal projection neurons, were found to play a critical role in modulating several important dopamine-dependent behaviors (Jeon, J. et al., *J. Neurosci.* 2010, 30, 6, 2396-2405). Based on those observations, we believe that our more functionally selective $M_1/M_4$ analogs may provide a viable approach for the treatment of certain central nervous system disorders including Parkinson (PD) (Dencker, D. et al. *ACS Chem. Neurosc.* 2012, 3, 2, 80-89). However, muscarinic antagonists may have somewhat limited clinical applications due to central and peripheral adverse effects associated with the blockage of multiple muscarinic subtypes that are not involved in the regulation of basal ganglia motor function.

Results

Chemistry Compound 6 (Scheme 1) was synthesized by reacting pyridine with 2-bromoethanol and then selectively reduced with sodium borohydride to produce compound 7 (Niu, Y. et al., Chin. J. Pharm. 2003, 34, 11, 541-578). Reaction of 7 with p-substituted benzoyl chlorides afforded compounds 8a-c which were then treated with hydrogen chloride gas and iodomethane to afford salts 9a-b and 10a-c, respectively. Compound 11 (Scheme 2) was formed by reacting piperidine with 2-bromoethanol and then treated with several p-substituted benzoyl chlorides to yield compounds 12a-b. Compounds 12a-b reacted with iodomethane and hydrogen chloride to produce the corresponding salts 13a-b and 14a-b, respectively.

Scheme 1. Synthesis of N-Substituted 4-Benzoyl Tetrahydropyridinyl Salts

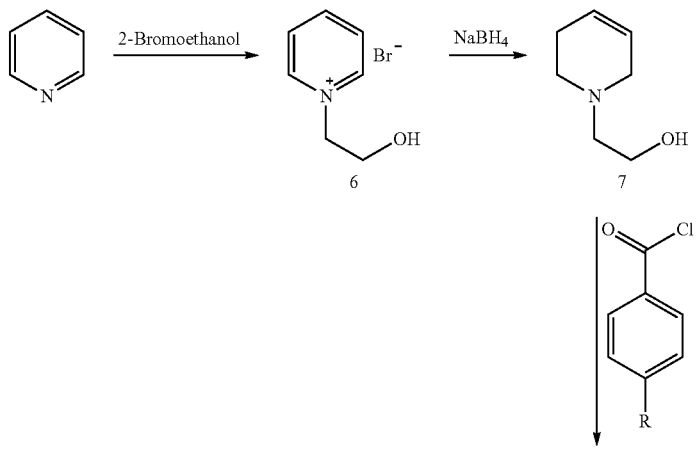

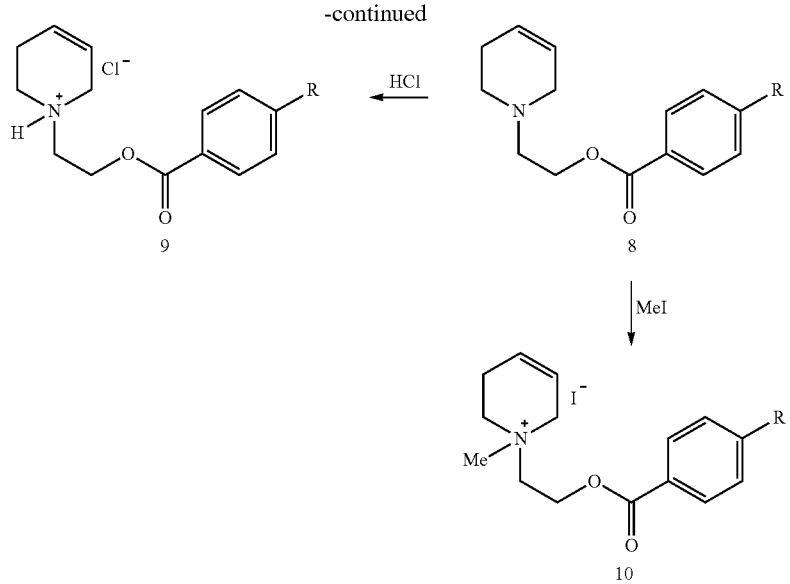

a: R= BuO, b: R= Bu, c: R= HexO

Scheme 2. Synthesis of N-Substituted p-Benzoyl Piperidinyl Salts

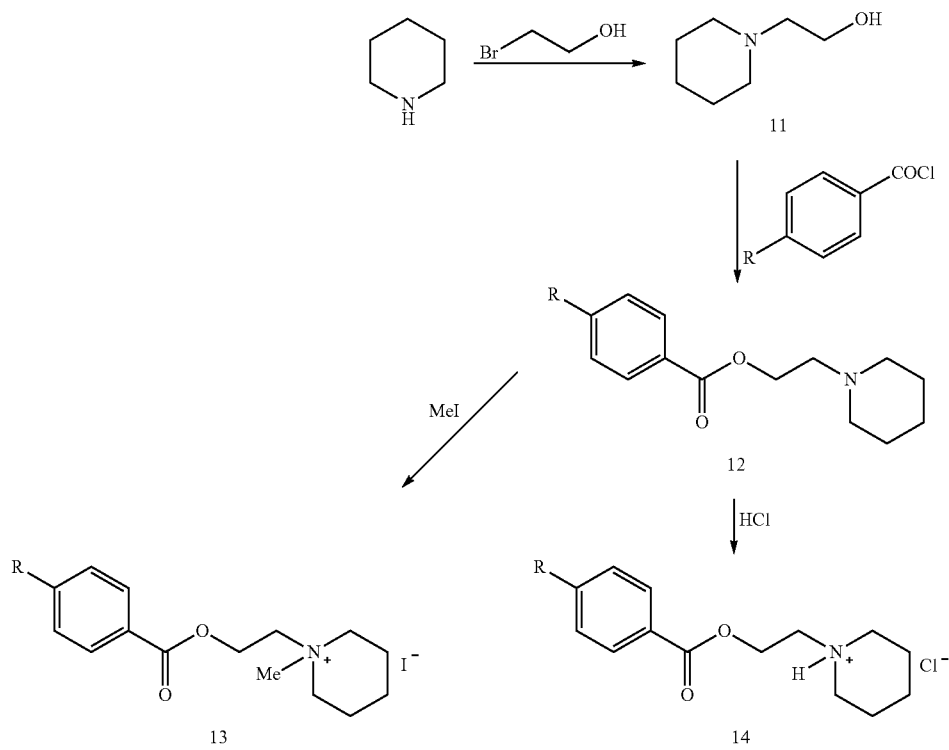

a: R= BuO, b: R= Bu

Biological Evaluation.

In equilibrium binding experiments, affinity of tested compounds (Schemes 1 and 2) was assessed in competition experiments with 1 nM [$^3$H]NMS. All tested compounds completely inhibited [$^3$H]NMS binding. Inhibition constants $K_I$ (expressed as $pK_I$), calculated according to equation 3 (data analysis section), are in micromolar range, Table 4. Tested compounds displayed the same affinity for all receptors with the following exceptions: Compound 13a displayed slightly (three to eight fold) higher affinity for $M_2$ receptor, 9a displayed slightly (two to four-fold) higher affinity for $M_2$ receptor, 9b displayed slightly (two to three-fold) higher affinity for $M_1$ receptor, 14b displayed slightly (two to five fold) higher affinity for the $M_2$ receptor, 13b displayed slightly (two to four fold) higher affinity for the $M_2$ receptor, and compound 10c displayed slightly higher affinity (one to three fold) for the $M_2$ and $M_5$ receptors. In general, analogs with a quaternary ammonium group bind with higher affinity than those with a tertiary cationic group at all receptor subtypes, 10b>9b, 10a>9a, and 13b>14b. Furthermore, compound 10c with a para-substituted hexoxy group (6-carbon alkoxy) displayed appreciably higher affinity than other compounds at all receptors.

TABLE 4

Binding Equilibrium Constants (expressed as $pK_I$)

| | $M_1$ | $M_2$ | $M_3$ | $M_4$ | $M_5$ |
|---|---|---|---|---|---|
| 9a | 5.2 ± 0.02 | 5.5 ± 0.1* | 5.1 ± 0.04 | 4.9 ± 0.1 | 5.2 ± 0.04 |
| 9b | 5.1 ± 0.1* | 4.7 ± 0.05 | 4.8 ± 0.1 | 4.6 ± 0.1 | 4.6 ± 0.2 |
| 10a | 5.6 ± 0.2 | 5.7 ± 0.2* | 5.2 ± 0.1 | 5.1 ± 0.1 | 5.5 ± 0.2 |
| 10b | 5.6 ± 0.1 | 5.6 ± 0.2 | 5.4 ± 0.1 | 5.4 ± 0.1 | 5.8 ± 0.1* |
| 10c | 6.5 ± 0.1 | 6.8 ± 0.1* | 6.4 ± 0.1 | 6.4 ± 0.1 | 6.8 ± 0.1* |
| 13a | 5.5 ± 0.02 | 6.04 ± 0.01* | 5.5 ± 0.01 | 5.1 ± 0.02 | 5.5 ± 0.05 |
| 13b | 5.5 ± 0.1 | 6.0 ± 0.1* | 5.69 ± 0.03 | 5.40 ± 0.1 | 5.61 ± 0.05 |
| 14b | 5.4 ± 0.1 | 5.7 ± 0.2* | 5.2 ± 0.04 | 5.01 ± 0.05 | 5.3 ± 0.2 |

Inhibition constants were calculated according to Eq. 3 and are expressed as negative logarithms;
*Higher than at other subtypes (P < 0.05); Values are means ± SD.

Ability of tested compounds to antagonize functional response at muscarinic receptors was determined in measurements of carbachol induced accumulation of inositol phosphates. Antagonism of tested compounds was determined at single high concentration of 0.1 mM. Compounds 9b and 10a lowered basal functional response (in the absence of carbachol) at all receptor subtypes, Table 5. Moreover, compounds 9a lowered basal functional response at $M_1$ and $M_5$ receptors and compound 10b at $M_3$ and $M_4$ receptors. Ability to inhibit basal functional response does not correlate with inhibition constants in Table 4.

TABLE 5

Effect of ligands at 0.1 mM concentration on basal activity

| | $M_1$ | $M_2$ | $M_3$ | $M_4$ | $M_5$ |
|---|---|---|---|---|---|
| 9a | 90 ± 2* | 100 ± 6 | 100 ± 1 | 100 ± 6 | 91 ± 2* |
| 9b | 85 ± 4* | 79 + 4* | 81 ± 5* | 73 ± 6* | 88 ± 3* |
| 10a | 83 ± 3* | 86 ± 5* | 74 ± 3* | 74 ± 7* | 89 ± 3* |
| 10b | 98 ± 9 | 102 ± 10 | 87 ± 4* | 75 ± 6* | 90 ± 10 |
| 10c | 101 ± 1 | 100 ± 2 | 101 ± 1 | 100 ± 2 | 101 ± 1 |
| 13a | 97 ± 2 | 101 ± 1 | 102 ± 2 | 98 ± 4 | 98 ± 3 |
| 13b | 104 ± 4 | 108 ± 4 | 104 ± 4 | 107 ± 4 | 104 ± 4 |
| 14b | 103 ± 3 | 106 ± 1 | 103 ± 3 | 106 ± 1 | 103 ± 3 |

Accumulation of inositol phosphates in the presence of the ligand is expressed as percent (%) of accumulation or binding in the absence of the ligand;
*different from basal activity in the absence of ligand (P < 0.05).
Values are means ± SD.

All tested compounds antagonized functional response to carbachol and increased carbachol half-efficient concentration ($EC_{50}$), Table 6. The strongest antagonism was observed for compounds 9b, 10a-c at $M_1$ receptors where they increased carbachol $EC_{50}$ by more than 1000 folds. In addition, 10c increased carbachol $EC_{50}$ by more than 1000 fold at $M_3$ and $M_5$ receptors. Such increase in $EC_{50}$ is substantially greater than can be expected for competitive antagonists with observed $K_I$. These compounds also increased $EC_{50}$ of carbachol more than expected for competitive antagonist at $M_4$ receptors. Compounds 13b and 14b increased the $EC_{50}$ of carbachol by 810 and 460 times at $M_1$ receptors, respectively. In addition 13b and 14b increased $EC_{50}$ of carbachol more than expected for competitive antagonists at $M_3$ and $M_5$ receptors.

TABLE 6

Effect of ligands at 0.1 mM concentration on half-efficient concentration ($EC_{50}$) of carbachol

| | $M_1$ | $M_2$ | $M_3$ | $M_4$ | $M_5$ |
|---|---|---|---|---|---|
| 9a | 1.9 ± 0.3 | 5.0 ± 0.5 | 2.5 ± 0.1 | 1.6 ± 0.1 | 3.1 ± 0.6 |
| 9b | >1000* | 5.3 ± 0.5 | 14 ± 3 | 194 ± 37* | 24 ± 7 |
| 10a | >1000* | 30 ± 4 | 17 ± 1 | 183 ± 36* | 36 ± 5 |
| 10b | >1000* | 26 ± 5 | 30 ± 8 | 196 ± 34* | 57 ± 17 |
| 10c | >1000* | 28 ± 4 | >1000* | 240 ± 30* | >1000* |
| 13a | 32 ± 3 | 52 ± 2 | 26 ± 8 | 23 ± 5 | 15 ± 2 |
| 13b | 810 ± 50* | 22 ± 3 | 70 ± 8* | 21 ± 4 | 140 ± 12* |
| 14b | 460 ± 40* | 27 ± 3 | 128 ± 5* | 23 ± 6* | 72 ± 6* |

Shift in $EC_{50}$ of carbachol induced accumulation of inositol phosphates in the presence of the ligand is expressed in folds;
*Greater than maximum possible shift based on competitive interaction and inhibition constant from Table 1 (P < 0.05, t-test).
Values are means ± SD.

Figure 5:
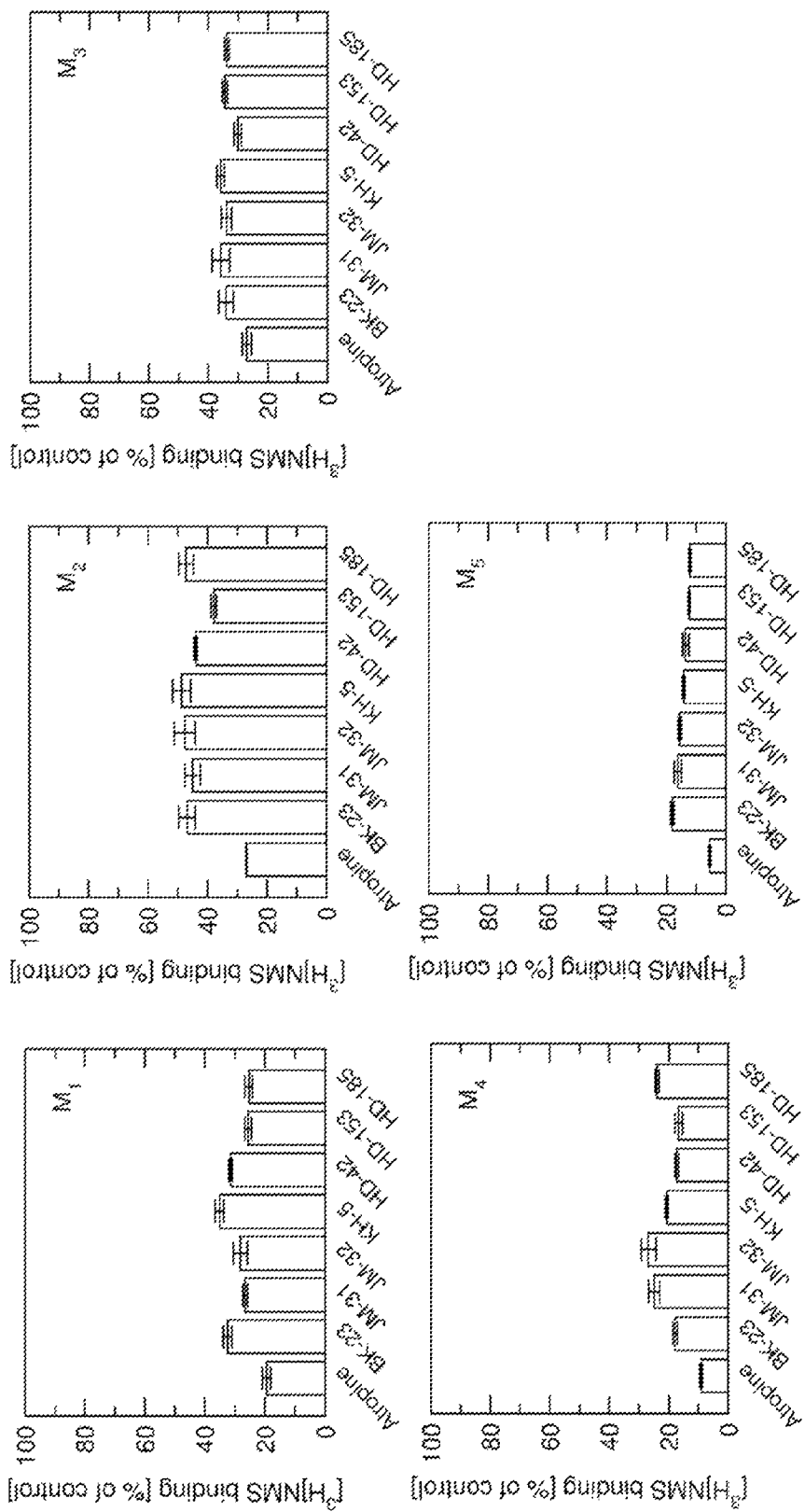
FIG. 5 is a series of graphs showing the effect of antagonists at 100 μM concentration on [$^3$H]NMS dissociation. Bars indicate [3H]NMS binding after 5 min ($M_2$), 30 min ($M_1$ and $M_3$), 40 min ($M_4$) or 2 hours of dissociation ($M_5$) invoked by atropine alone or in mixture with antagonist expressed as percent of binding in the beginning of dissociation. Bars are means±S.D. from 3 independent experiments performed in quadruplicates.

All Compounds slowed down in [$^3$H]NMS dissociation as seen in FIG. 5.

The major finding of this study is the identification of $M_1/M_4$ functionally selective muscarinic antagonists. All five muscarinic receptor subtypes share high sequence homology, especially at the orthosteric binding site. Current crystallographic structures of $M_2$ and $M_3$ receptors show that homology in the secondary and tertiary structure extends even beyond the orthosteric binding site (Haga, K. et al. *Nature*. 2012, 482, 547-551). This high homology hinders the discovery of ligands that bind selectively to specific receptor subtypes. Various functionally selective muscarinic ligands (ligands that preferentially activate only some receptor subtypes or signaling pathways) that bind to all receptor subtypes with the same affinity are discussed. Functionally selective ligands thus appear to be possible ways for selective modulation of function of muscarinic receptors.

Novel compounds bind to all receptor subtypes with the same affinity, Table 4. Complete inhibition of the orthosteric antagonist [$^3$H]NMS suggests steric interaction (mutual exclusivity of binding) between compounds and [$^3$H]NMS. On the other hand, in some cases, antagonism of carbachol induced functional response by compounds suggests non-competitive interaction with carbachol as shifts in carbachol $EC_{50}$ are greater than can be expected for competitive antagonism based on their inhibition constants of [$^3$H]NMS binding and the assumption of no receptor reserve, Table 6. This discrepancy can be explained by existence of the secondary binding site (or mode) to which novel compounds bind with higher affinity than to the orthosteric binding site. From this secondary site, these compounds block receptor activation but do not inhibit [$^3$H]NMS binding. The existence of the secondary binding site is supported by slowdown in [$^3$H]NMS dissociation, FIG. 5, as any change of the ligand kinetics is conditioned by concurrent binding of two ligands to the receptor and concurrent binding of two ligands may occur only to two distinct sites.

Antagonism of 9b, 10a-b at $M_1$ receptors is stronger than at $M_4$ receptors and much stronger than at the rest of subtypes, Table 6. So these compounds are $M_1/M_4$ functionally selective antagonists. Antagonism of 10c at $M_1$, $M_3$ and $M_5$ receptors is stronger than at $M_4$ and much stronger than at $M_2$ receptors. Antagonism of 13b and 14b at $M_1$ receptors is stronger than at $M_3$ and $M_5$ receptors and much stronger than at other two subtypes. Thus 14b is an $M_1/M_3$ functionally selective antagonist whereas 13b is $M_1/M_5$ functionally selective. Moreover, compounds 9a-b, 10a-b behave as inverse agonists. They lower basal accumulation of inositol phosphates in the absence of agonist (carbachol), Table 5. Observed inverse agonism varies among compounds as well as receptor subtypes as it does not correlate with inhibition constants ($K_I$) in Table 4. The lack of correlation between inverse agonism and $K_I$ suggests that the lack of inverse agonism is not due to lower (insufficient) receptor occupancy. Rather the inverse agonism of tested compounds is system dependent. Taken together, compounds 9b, 10a-b are $M_1/M_4$ selective dual-steric non-competitive inverse agonists.

Experimental Methods

General Procedures.

Reagents were purchased from Aldrich Chemical Company (St. Louis, Mo.) unless otherwise noted, and all starting liquid materials were distilled before use. NMR spectra were recorded on a Varian 300 MHz spectrometer. GC-MS spectra were recorded on a Perkin Elmer Clarus 500 and 560S system. Elemental analyses were carried out by Galbraith Laboratories (Knoxville, Tenn.) and biological assays were conducted by Jan Jakubik at the Institute of Physiology of the Czech Academy of Sciences in Prague. Melting points were recorded on a Digimelt MPA160 purchased from Stanford Research Systems and are uncorrected. Refractive indexes were recorded on $r^2$ i300 digital refractometer from Reichert Technologies corrected for 20° C. The radioligands [$^3$H]-N-methylscopolamine chloride ([$^3$H]-NMS), and [$^3$H]-myo-inositol were purchased from American Radiolabeled Chemicals (St. Louis, Mo., USA). Carbachol, dithiothreitol, ethylendiaminotetraacetic acid (EDTA), and N-methylscopolamine chloride (NMS) were purchased from Sigma (St. Louis, Mo., USA).

1-(2-hydroxyethyl)pyridinium bromide (6)

A solution of 10.07 g of 2-bromoethanol (0.0805 mol) in 20 mL of acetonitrile was added slowly to another solution containing 6.36 g of pyridine (0.0804 mol) and 20 mL of acetonitrile. After addition, the mixture was allowed to stir for 6 days and then refluxed for one hour. The mixture was then concentrated and residue recrystallized from n-butanol to yield 11.79 g (72.3%) of white crystals, m.p. 102.5-103.0° C. $^1$H-NMR ($D_2O$): δ 8.75 (2H, d), 8.45 (1H, t), 7.95 (2H, t), 4.6 (2H, t), 3.9 (2H, t). MS (m/z): 79.01 base [$C_5H_5N$]$^+$.

1-(2-hydroxyethyl)-1,2,5,6-tetrahydropyridine (7)

To a mixture containing 7.10 g of 6 (0.0348 mol) and 100 mL of methanol, a solution of sodium borohydride (5.25 g, 0.139 mol) in 60 mL of 0.1 M sodium hydroxide was added slowly with external cooling (ice-bath). The mixture was then allowed to stir at room temperature for an additional 30 minutes. 6 M hydrochloric acid was added to pH 5 and the solution was then brought to pH 8 with 3 M of sodium hydroxide. The mixture was extracted with dichloromethane, dried over anhydrous magnesium sulfate and concentrated to yield 1.24 g (28.0%). $^1$H-NMR ($CD_3COCD_3$): δ5.75 (1H, m), 5.65 (1H, m), 4.0-4.2 (1H, bs), 3.7 (2H, t), 3.05 (2H, t), 2.65 (4H, m), 2.15 (2H, m). MS (m/z): $M^+$ 127.08, 96.03 base [$C_6H_{10}N$]$^+$, 82.00 [$C_5H_8N$]$^+$.

2-(1,2,5,6-tetrahydropyridine-N-ethyl)-4-butoxybenzoate 8(a)

2.07 g of 4-butoxy benzoylchloride (0.00974 mol) in 5 mL of diethyl ether was added slowly to a solution of 7 (1.24 g, 0.00974 mol) in 10 mL of anhydrous ether and 1.0 gram (0.0094 mol) of sodium carbonate. The mixture was stirred at room temperature for one hour. Diethyl ether was added and the excess carbonate was filtered off. The filtrate was adjusted to pH 8 with 6 M sodium hydroxide and the mixture extracted with ether. Combined ether extracts was dried over magnesium sulfate and concentrated to afford 1.84 g (62.4%). $^1$H-NMR ($CDCl_3$): δ 7.9 (2H, d), 6.9 (2H, d), 6.9 (1H, m), 6.7 (1H, m), 4.7 (2H, t), 4.0 (2H, t), 3.5 (2H, t), 3.2 (2H, d), 3.1 (2H, t), 2.4 (2H, m), 1.8 (2H, m), 1.5 (2H, m), 1.0 (3H, t). MS (m/z): $M^+$ 303.18, 96.05 base [$C_6H_{10}N$]$^+$, 109.05 [$C_7H_{11}N$]$^+$, 82.00 [$C_5H_8N$]$^+$.

2-(1,2,5,6-tetrahydropyridine-N-ethyl)-4-butoxybenzoate hydrochloride 9(a)

Hydrogen chloride gas was bubbled through a solution containing 0.50 g (0.00165 mol) of 8a and 5 mL of acetonitrile. The solution was concentrated to afford 0.55 g of a solid residue. The solid was recrystallized from n-butanol to yield 0.42 g (75.0%), m.p. 145-147° C. $^1$H-NMR (D20): δ 7.8 (2H, d), 6.9 (2H, d), 5.8 (1H, m), 5.5 (1H, m), 4.5 (2H, t), 3.9 (2H, d), 3.7 (2H, t), 3.5 (2H, t), 3.3 (2H, t), 2.3 (2H, m), 1.6 (2H, m), 1.3 (2H, m), 0.7 (3H, t). Elemental analysis calculated (%) for $C_{18}H_{26}NO_3Cl$ ($H_2O$): C, 60.44; H, 7.83; N, 3.91; Cl, 9.91. Found: C, 60.58; H, 7.34; N, 3.76; Cl, 10.02.

2-(1,2,5,6-tetrahydropyridine-N-ethyl)-4-butoxybenzoate N-methyl iodide 10(a)

To a solution of 1.00 g of 8a (0.0033 mol) in 10 mL of acetonitrile, 0.57 g of methyl iodide (0.00395 mol) was added and stirred overnight. The mixture was concentrated and the residue washed with anhydrous ether to promote crystallization. The resulting salt was recrystallized from n-hexanol and vacuum dried to yield 1.037 g (70.45%) of an off-white powder, m.p. 99-100° C. $^1$H-NMR ($D_2O$): δ 7.9 (2H, d), 6.9 (2H, d), 5.9 (1H, m), 5.6 (1H, m), 4.6 (2H, t), 4.0 (2H, t), 3.7 (2H, d), 3.6 (2H, t), 3.5 (2H, t), 3.1 (3H, s), 2.4 (2H, m), 1.6 (2H, m), 1.4 (2H, m), 0.9 (3H, t). Elemental analysis calculated (%) for $C_{19}H_{28}NO_3I$: C, 51.24; H, 6.34; N, 3.15; I, 28.50. Found: C, 50.80; H, 6.18; N, 2.92; I, 28.72.

2-(1,2,5,6-tetrahydropyridine-N-ethyl)-4-butylbenzoate 8(b)

Reagents used: 1.16 g of 4-butyl benzoylchloride (0.0059 mol) dissolved 3 mL of anhydrous ether, 0.75 g of 7 (0.0059 mol) dissolved in 3 mL of anhydrous ether, one gram of sodium carbonate (0.0094 mol). 1.5 g was recovered (89%). Purity was determined by GC-MS. $^1$H-NMR (CDCl$_3$) δ7.95 (2H, d), 7.3 (2H, d), 5.7 (1H, m), 5.65 (1H, m), 4.5 (2H, t), 3.1 (2H, d), 2.9 (2H, t), 2.7 (2H, t), 2.6 (2H, m), 2.2 (2H, t), 1.6 (2H, m), 1.35 (2H, m), 0.9 (3H, t). MS (m/z): M$^+$ 287.13, 161.12 $[C_{11}H_{13}O]^+$, 109.11 $[C_5H_8N]^+$, 96.06 base $[C_6H_{10}N]^+$, 82.03 $[C_5H_8N]^+$.

2-(1,2,5,6-tetrahydropyridine-N-ethyl)-4-butylbenzoate hydrochloride 9(b)

Reagents used: 0.5 g (0.00174 mol) of 8b, hydrogen chloride, 5 mL of acetonitrile. Solid residue was recrystalized from a mixture of n-butanol, carbon tetrachloride and ether to afford 0.402 g (71.4%), mp 115.3-116.5° C. The sample was first dissolved in just enough warm 1-butanol, carbon tetrachloride was added to double the volume. This mixture was then cooled and anhydrous diethyl ether was added until solution turned cloudy with white crystals precipitating out with further cooling. $^1$H-NMR (D$_2$O): δ7.8 (2H, d), 7.25 (2H, d), 5.85 (1H, m), 5.6 (1H, m), 4.56 (2H, t), 3.8 (2H, t), 3.7 (2H, d), 3.54 (2H, t), 2.55 (2H, t), 2.3 (2H, m), 1.45 (2H, m), 1.15 (2H, m), 0.75 (3H, t). Elemental analysis calculated (%) for $C_{18}H_{26}NO_2Cl$ (H$_2$O): C, 66.76; H, 8.09; N, 4.33; Cl, 10.95. Found: C, 66.59; H, 7.99; N, 4.32; Cl, 10.83.

2-(1,2,5,6-tetrahydropyridine-N-ethyl)-4-butylbenzoate N-methyl iodide 10(b)

A solution containing 0.86 g (0.0030 mol) of 8(b), 0.509 g (0.00448 mol) of CH$_3$I and 5 ml of acetonitrile was stirred at room temperature overnight. The solution was concentrated and solid recrystallized from n-butanol to yield 0.96 g (75%), mp 110.3-111.6° C. $^1$H-NMR (D$_2$O) δ7.8 (2H, d), 7.2 (2H, d), 5.9 (1H, m), 5.5 (1H, m), 4.0 (2H, d), 3.8 (2H, m), 3.7 (2H, t), 3.5 (2H, t), 3.1 (3H, s), 2.6 (2H, t), 2.4 (2H, m), 1.5 (2H, m), 1.1 (2H, m), 0.7 (3H, t). Elemental analysis calculated (%) for $C_{19}H_{28}NO_2I$: C, 53.15%; H, 6.57%; N, 3.26%; I, 29.56. Found: C, 52.85%; H, 6.44%; N, 3.22%; I, 29.63%.

2-(1,2,5,6-tetrahydropyridine-N-ethyl)-4-hexoxybenzoate 8(c)

Reagents used: 1.022 g of 4-hexoxy benzoylchloride (0.00425 mol) dissolved 5 mL of anhydrous ether, 0.54 g of 7 (0.00425 mol) dissolved in 5 mL of anhydrous ether, one gram of sodium carbonate (0.0094 mol). 0.94 g of was recovered (67.1%). Purity was determined by GC-MS. $^1$H-NMR (CD$_3$COCD$_3$) δ7.95 (2H, d), 7.05 (2H, d), 5.7-5.6 (2H, m), 4.0 (2H, t), 4.1 (2H, t), 3.1 (2H, d), 2.8 (2H, t), 2.7 (2H, t), 2.1 (2H, m), 1.8 (2H, m), 1.5 (2H, m), 1.4 (4H, m), 0.9 (3H, t). MS (m/z): M$^+$ 331.18, 205.16 $[C_{13}H_{17}O_2]^+$, 109.14 $[C_7H_{11}N]^+$, 96.07 base $[C_6H_{10}N]^+$, 82.02 $[C_5H_8N]^+$.

2-(1,2,5,6-tetrahydropyridine-N-ethyl)-4-hexoxybenzoate N-methyl iodide 10(c)

A solution containing 0.47 g (0.00142 mol) of 8c, 1.14 g (0.0074 mol) of CH$_3$I and 5 ml of acetonitrile was stirred at room temperature overnight. The solution was concentrated and solid residue recrystallized from n-butanol to yield 0.46 g (69%), mp 107.5-108.5° C. $^1$H-NMR (CD$_3$COCD$_3$) δ8.1 (2H, d), 7.1 (2H, d), 6.1 (1H, m), 5.9 (1H, m), 4.9 (2H, t), 4.4 (2H, dd), 4.3 (2H, t), 4.0 (2H, t), 3.6 (2H, t), 2.8 (3H, s), 2.7 (2H, m), 2.1 (2H, m), 1.8 (2H, m), 1.5 (2H, m), 1.4 (2H, m), 0.9 (3H, t). Elemental analysis calculated (%) for $C_{21}H_{32}NO_3I$: C, 53.31%; H, 6.76%; N, 2.96%; I, 26.82. Found: C, 52.88%; H, 6.66%; N, 2.98%; I, 29.87%.

1-(2-hydroxyethyl)piperidine (11) To a mixture containing 10.38 g of piperidine (0.122 mol), 10.818 g of sodium carbonate (0.122 mol) and 50 mL of acetonitrile was added slowly another mixture containing 15.25 g of 2-bromoethanol (0.121 mol) and 50 mL of acetonitrile. The reaction mixture was allowed to stir for 7 additional days at room temperature. The mixture was then concentrated and the residue washed several times with ether. Ether solution was concentrated and residue distilled to afford 5.15 g (33.0%), colorless liquid, by 59° C./5 mm Hg, $n_D$ 1.4787. MS m/z: M$^+$ 129.03, 98.06 base $[C_6H_{12}N]^+$, 31 $[CH_2=OH]^+$. Literature value: by 70-75/10 mm Hg, $n_D$ 1.4794. $^1$H-NMR (CD$_3$COCD$_3$): δ 1.40-1.45 (2H, m), 1.5-1.6 (4H, m), 2.45-2.40 (6H, m), 3.55 (2H, t).

2-(N-Piperidine ethyl) p-butylbenzoate 12(b)

A solution of 0.50 g (0.0039 mol) of 11 in 5 mL of acetonitrile was added to another mixture containing 0.76 g of 4-butyl benzoyl chloride (0.0039 mol), 0.50 g of sodium carbonate (0.00472 mol) and 5 mL of acetonitrile. After 2 hours of stirring, at room temperature, the sodium carbonate was filtered off and filtrate then made alkaline with 6 M sodium hydroxide to pH 8. The mixture was then extracted with ether, dried over magnesium sulfate and concentrated to afford 0.605 g (54%). $^1$H-NMR (CD$_3$COCD$_3$): δ 7.95 (2H, d), 7.35 (2H, d), 4.4 (2H, t), 2.7 (4H, m), 2.5 (4H, m), 1.65 (2H, m), 1.55 (4H, m), 1.4 (4H, m), 0.9 (3H, t). MS (m/z): M$^+$ 289, 205.25 $[C_{13}H_{17}O_2]^+$, 98.17 base $[C_6H_{12}N]^+$, 111.17 $[C_7H_{13}N]^+$.

2-(N-Piperidine ethyl) p-butylbenzoyl ester N-methyl iodide 13(b)

0.80 mL of iodomethane (0.013 mol) was added to a mixture of 0.30 g of 12b (0.00104 mol) dissolved in 6 mL of dichloromethane. The solution was allowed to stand overnight at room temperature, concentrated to yield a solid residue. The solid was then recrystallized from a mixture of n-butanol and ether to yield 0.245 g (54.4%), mp 113.3-114.7° C. $^1$H-NMR (D$_2$O): δ 8.0 (2H, d), 7.4 (2H, d), 4.9 (2H, t), 4.25 (2H, t), 3.9 (4H, t), 2.8 (3H, s), 2.75 (2H, t), 2.1 (6H, m), 1.6 (2H, m), 1.4 (2H, m), 1.0 (3H, t). Elemental analysis calculated (%) $C_{19}H_{30}NO_2I$: C, 52.93; H, 6.96; N, 3.25; I, 29.44. Found: C, 52.67; H, 7.14; N, 3.18; I, 30.17.

2-(N-Piperidine ethyl) p-butylbenzoyl ester N-methyl iodide 14(b)

HCl gas was passed through a mixture of 0.30 g of 12b (0.001014 mol) for several minutes. The solution was concentrated to afford 0.39 g of a solid residue. The solid was then recrystallized from a mixture of n-butanol and ether to yield 0.136 g (40.0%), mp 159.6-160.8° C. $^1$H-NMR (D$_2$O): δ 7.8 (2H, d), 7.3 (2H, d), 4.5 (2H, t), 3.5 (4H, m), 3.0 (2H, bm), 2.6 (2H, t), 2.75 (2H, t), 1.8-1.6 (6H, m), 1.45 (2H, m), 1.2 (2H, m), 0.75 (3H, t). Elemental analysis calculated (%)

for $C_{18}H_{28}NO_2Cl$: C, 66.39; H, 8.60; N, 4.30; Cl, 10.89. Found: C, 66.24; H, 8.36; N, 4.33; Cl, 10.74.

Cell Culture and Membrane Preparation

Chinese hamster ovary cells stably transfected with the genes of human variants of muscarinic receptors were purchased from Missouri S&T cDNA Resource Center (Rolla, Mo., USA). Cell lines expressing $M_2$ and $M_4$ receptors were transfected with cDNA coding $G_{16}$ G-protein (Missouri S&T cDNA Resource Center, Rolla, Mo., USA) to couple them to phospholipase C (Milligan, G., et al., *Trends Pharmacol Sci.* 1996, 17, 235-237). Cell cultures and crude membranes were prepared as described previously (Jakubik, J. et al., *Mol. Pharmacol.* 2006, 70, 656-666). Cells were grown to confluency in 75 cm² flasks in Dulbecco's modified Eagle's medium supplemented with 10% fetal bovine serum and 2 million of cells were subcultured to 100 mm Petri dishes. Medium was supplemented with 5 mM butyrate for the last 24 hours of cultivation to increase receptor expression. Cells were detached by mild trypsinization on day 5 after subculture. Detached cells were washed twice in 50 mL of phosphate-buffered saline and 3 min centrifugation at 250×g. Washed cells were suspended in 20 mL of ice-cold homogenization medium (100 mM NaCl, 20 mM Na-HEPES, 10 mM EDTA, pH=7.4) and homogenized on ice by two 30 s strokes using Polytron homogenizer (Ultra-Turrax; Janke & Kunkel GmbH & Co. KG, IKA-Labortechnik, Staufen, Germany) with a 30 s pause between strokes. Cell homogenates were centrifuged for 5 min at 1,000×g and resulting supernatants were centrifuged for 30 min at 30,000×g. Supernatants from heavy centrifugation were discarded, pellets suspended in incubation medium (100 mM NaCl, 20 mM Na-HEPES, 10 mM $MgCl_2$, pH=7.4), incubated on ice for 30 minutes and centrifuged again. Resulting membrane pellets were kept at −80° C. until assayed within 10 weeks at a maximum.

Radioligand Binding Experiments.

All radioligand binding experiments were optimized and carried out as described earlier. Briefly, membranes were incubated in 96-well plates at 30° C. in the incubation medium described. Incubation volume was 400 μL or 800 μL for competition and saturation experiments with [³H] NMS, respectively. Approximately 30 μg of membrane proteins per sample were used for [³H]NMS binding. N-methylscopolamine binding was measured directly in saturation experiments using six concentrations (30 pM to 1000 pM) of [³H]NMS for 1 hour (3 hours in case of $M_5$ receptors). For calculations of equilibrium dissociation constant ($K_D$), concentrations of free [³H]NMS were calculated by subtraction of bound radioactivity from total radioactivity in the sample and fitting Eq. 1 (see Data Analysis subsection below) to the data. Binding of tested ligands was determined in competition experiments with 1 nM [³H]NMS for 3 hours (5 hours in case of $M_5$ receptors) and inhibition constant $K_I$ was calculated according Eq. 3 (see Data Analysis subsection below). Effect of tested ligands on [³H]NMS dissociation was determined after 1 hour ($M_2$ receptors), 3 hours ($M_1$, $M_3$ and $M_4$ receptors) or 5 hours ($M_5$ receptors) of pre-incubation of membranes with 1 nM [³H]NMS and subsequent 5 min ($M_2$ receptors), 30 min ($M_1$ and $M_3$ receptors) 40 min ($M_4$ receptors) or 2 hours of dissociation ($M_5$ receptors). Dissociation was initiated by addition of atropine to final concentration of 5 Tested ligands in final concentration of 100 μM were added concurrently with atropine. Incubations were terminated by filtration through Whatman GF/C glass fiber filters (Whatman) using a Brandel cell harvester (Brandel, Gaithersburg, Md., USA). Filters were dried in vacuum for 1 h while heated at 80° C. and then solid scintillator Meltilex A was melted on filters (105° C., 90 s) using a hot plate. The filters were cooled and counted in Wallac Microbeta scintillation counter.

Accumulation of Inositol Phosphates.

Accumulation of inositol phosphates was measured according to Michal et al. (*Eur. J. Pharmacol.* 2009, 606, 50-60). Inositolphosphates formation was determined in cells pre-labeled overnight by 0.5 μM [³H]myo-inositol in 0.3 mL of DMEM (3 μCi/ml) at 37° C. Cells were then washed with Krebs-HEPES buffer (KHB) (138 mM NaCl, 4 mM KCl, 1.3 mM $CaCl_2$, 1 mM $NaH_2PO_4$, 20 mM Na-HEPES, 10 mM glucose, pH=7.4) and pre-incubated in 0.4 mL of KHB containing 10 mM LiCl for 15 min at 37° C. Then agonist carbachol±tested compound was added and samples were incubated for additional 20 min in final volume 0.5 mL. Incubation was stopped by removal of incubation buffer and addition 0.2 mL 20% trichloracetic acid (TCA). After 1 h incubation at 4° C., 100 μL, of TCA extracts were taken for measurement. Rest of the TCA was removed, and TCA precipitates were washed with 200 μL TCA and dissolved in 200 μL of 1 M NaOH. After 1 h incubation at 4° C., 100 μL, of NaOH lysates were taken for measurement. Radioactivity in TCA extracts and NaOH lysates were determined by liquid scintillation counting. The rate of inositolphosphates accumulation was calculated as a percentage of the soluble (released) inositolphosphates from the total incorporated radioactivity (sum of radioactivity in NaOH lysates and TCA extracts).

Data Analysis.

Data from biological evaluation experiments were processed in Libre Office, than analyzed and plotted using program Grace (Grace Development Team Grace: A plotting tool. 2014). Statistical analysis was performed using statistical package R (R Core Team, 2014) (R Core Team: A Language and Environment for Statistical Computing. *R Foundation for Statistical Computing*, Vienna, Austria. 2014). For non-linear regression analysis following equations were used:

[³H]NMS saturation binding $$y = \frac{B_{MAX} * x}{x + K_D} \quad \text{Eq. 1}$$

where y is specific binding at free concentration x, $B_{MAX}$ is maximum binding capacity, and $K_D$ is equilibrium dissociation constant.

Competition binding $$y = 100 - \frac{100 * x}{x + IC_{50}} \quad \text{Eq. 2}$$

where y is specific radioligand biding at concentration x of competitor expressed as percent of binding in the absence of competitor, $IC_{50}$ is concentration causing 50% inhibition of radioligand binding. Inhibition constant $K_I$ was calculated as:

$$K_I = \frac{IC_{50}}{1 + \frac{[D]}{K_D}} \quad \text{Eq. 3}$$

where $IC_{50}$ is concentration causing 50% inhibition of [3H] NMS binding calculated according Eq. 2 from competition binding data, [D] is concentration of [$^3$H]NMS used, and $K_D$ is its equilibrium dissociation constant calculated according Eq. 1 from saturation binding data (Cheng, Y. et al., *Biochem. Pharmacol.* 1973, 22, 3099-3108).

Concentration response $$y = 1 + \frac{(E_{MAX} - 1) * x^{nH}}{x^{nH} + EC_{50}^{nH}} \qquad \text{Eq. 4}$$

where y is response normalized to basal (in the absence of carbachol) at ligand concentration x, $E_{MAX}$ is maximal effect, $EC_{50}$ is concentration causing half-maximal effect, and nH is Hill coefficient.

Characterization of CHO Cells.

Equilibrium dissociation constants ($K_D$) and maximum binding capacities ($B_{MAX}$) of [$^3$H]NMS were obtained by fitting Eq.1 to the data from saturation binding experiments. $K_D$ values are expressed as negative logarithms and $B_{MAX}$ values as pmol of binding sites per mg of membrane protein. Half-efficient concentrations ($EC_{50}$) and maximal effects ($E_{MAX}$) of carbachol were obtained by fitting Eq. 4 to the data from measurements of accumulation of inositol phosphates. $EC_{50}$ values are expressed as negative logarithms and $E_{MAX}$ values as folds over basal, Table 7.

TABLE 7

Binding and Activation Parameters of CHO cells

| | [$^3$H]NMS | | carbachol | |
|---|---|---|---|---|
| | $pK_D$ | $B_{MAX}$ [pmol/mg] | $pEC_{50}$ | $E_{MAX}$ [fold over basal] |
| $M_1$ | 9.60 ± 0.04 | 1.8 ± 0.2 | 5.7 ± 0.1 | 3.6 ± 0.2 |
| $M_2$ | 9.43 ± 0.05 | 1.3 ± 0.2 | 6.5 ± 0.1 | 4.4 ± 0.1 |
| $M_3$ | 9.64 ± 0.04 | 1.7 ± 0.2 | 5.9 ± 0.1 | 3.1 ± 0.2 |
| $M_4$ | 9.66 ± 0.05 | 0.9 ± 0.1 | 5.5 ± 0.2 | 3.3 ± 0.3 |
| $M_5$ | 9.52 ± 0.05 | 1.0 ± 0.1 | 5.7 ± 0.1 | 2.5 ± 0.2 |

TABLE 8

Structures of Bitopic Muscarinic Antagonists

General Formula (ring B, mono-unsaturated)

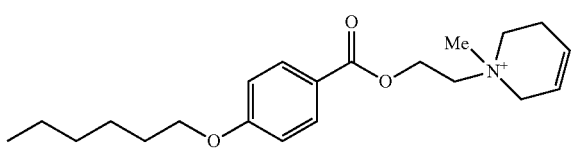

Ring A
KH-5 ($R_1$ = Hexyl, $R_2$ = Me, Z = O, X = C, Y = O, n = 2)

Ring B

TABLE 8-continued

Structures of Bitopic Muscarinic Antagonists

BK-23 ($R_1$ = Butyl, $R_2$ = H, , Z = O, X = C, Y = O, n = 2)

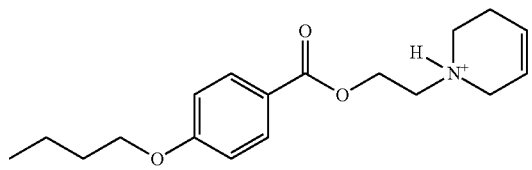 [SMILES: CCCCOc1ccc(C(=O)OCC[NH+]2CC=CCC2)cc1]

HD-42 ($R_1$ = Butyl, $R_2$ = Me, , Z = O, X = C, Y = O, n = 2)

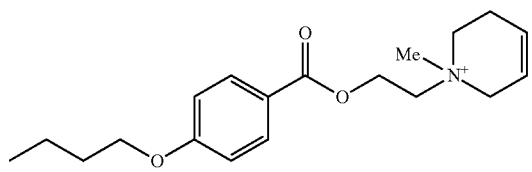 [SMILES: CCCCOc1ccc(C(=O)OCC[N+]2(C)CC=CCC2)cc1]

HD-153 ($R_1$ = Propyl, $R_2$ = H, , Z = $CH_2$, X = C, Y = O, n = 2)

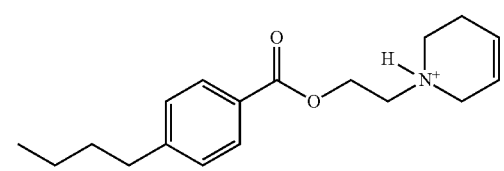 [SMILES: CCCCc1ccc(C(=O)OCC[NH+]2CC=CCC2)cc1]

HD-185 ($R_1$ = Propyl, $R_2$ = Me, Z = $CH_2$, X = C, Y = O, n = 2)

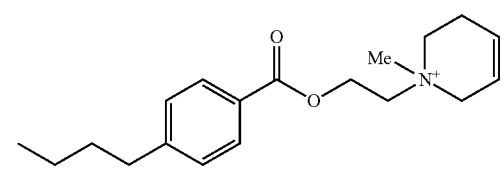

TABLE 9

Structures of Bitopic Muscarinic Antagonists

General Formula (ring B, Saturated)

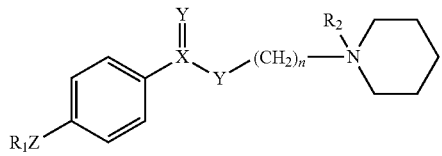

Ring A
JM-31 ($R_1$ = Propyl, $R_2$ = H, Z = $CH_2$, X = C, Y = O, n = 2)

Ring B

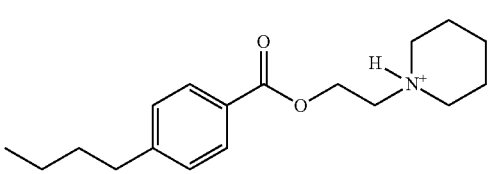 [SMILES: CCCCc1ccc(C(=O)OCC[NH+]2CCCCC2)cc1]

TABLE 9-continued

Structures of Bitopic Muscarinic Antagonists

JM-32 ($R_1$ = Propyl, $R_2$ = Me, , Z = $CH_2$, X = C, Y = O, n = 2)

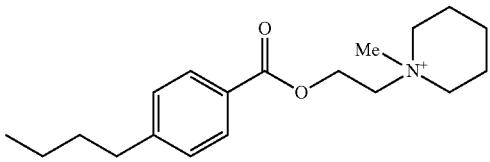 [SMILES: CCCCc1ccc(C(=O)OCC[N+]2(C)CCCCC2)cc1]

Referring to the compounds shown in Tables 8 and 9, these compounds and analogs and derivatives thereof can be used for treating a condition associated with modulation of a muscarinic receptor (e.g., one or more of $M_1$, $M_2$, $M_3$, $M_4$, $M_5$) as described above for all other compounds (e.g., JB-D4)—as neuromuscular blocking agents (e.g., for use in compositions for anesthetizing a subject), for the treatment of CNS disorders (e.g., Parkinson's disease, Schizophrenia, etc.), OAB syndrome, COPD, asthma, and many other diseases associated with the activation or inhibition of $M_1$-$M_5$ acetylcholine receptors, while providing, due to their bitopic nature, increased selectivity and efficacy compared to currently available therapeutics. Compounds with $R_2$=H are able to cross the blood-brain barrier and may be used to treat neurological diseases including AD (agonists including e.g., $M_1$, $M_5$ or $M_1$/$M_5$ mixed agonists, M2 antagonists), PD (antagonists including e.g., $M_1$, $M_4$ or $M_1$/$M_4$ mixed antagonists), Schizophrenia (agonists including e.g., $M_1$, $M_4$ or $M_1$/$M_4$ mixed agonists) and drug addiction (compounds with $R_2$=H ($M_5$ antagonists). Compounds with $R_2$=$CH_3$ (which are not able to cross the blood-brain barrier) can be used for peripheral diseases including peptic ulcer, chronic obstructive pulmonary disease, and irritable bowel. Compounds with $R_2$=H and $R_2$=Me (e.g., $M_1$-$M_5$ antagonists) can be used for (as) local and general anesthesia. The compounds in Tables 8 and 9 are antagonists, but analogs and/or derivatives thereof that are agonists can be synthesized and used according to the methods in this application and used to treat these and other diseases.

Other Embodiments

Any improvement may be made in part or all of the compositions, kits, and method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

The invention claimed is:

1. A composition comprising a pharmaceutically acceptable carrier and a bitopic muscarinic antagonist having the formula:

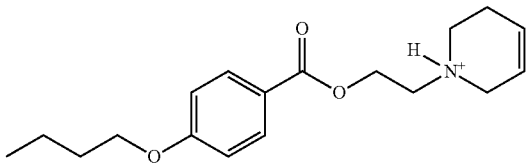 [SMILES: CCCCOc1ccc(C(=O)OCC[NH+]2CC=CCC2)cc1]

in a therapeutically effective amount for inhibiting activation of at least one muscarinic receptor selected from the group consisting of: $M_1$, $M_2$, $M_3$, $M_4$, and $M_5$ in a subject.

2. A composition comprising a pharmaceutically acceptable carrier and a bitopic muscarinic antagonist having the formula:

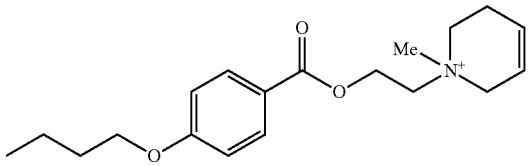

in a therapeutically effective amount for inhibiting activation of at least one muscarinic receptor selected from the group consisting of: $M_1$, $M_2$, $M_3$, $M_4$, and $M_5$ in a subject.

3. A composition comprising a pharmaceutically acceptable carrier and a bitopic muscarinic antagonist having the formula:

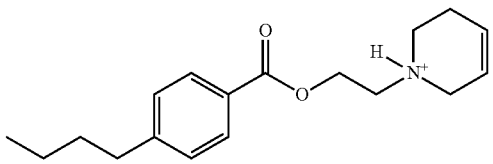 [SMILES: CCCCc1ccc(C(=O)OCC[NH+]2CC=CCC2)cc1]

in a therapeutically effective amount for inhibiting activation of at least one muscarinic receptor selected from the group consisting of: $M_1$, $M_2$, $M_3$, $M_4$ and $M_5$ in a subject.

4. A composition comprising a pharmaceutically acceptable carrier and a bitopic muscarinic antagonist having the formula:

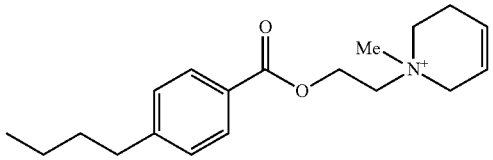 [SMILES: CCCCc1ccc(C(=O)OCC[N+]2(C)CC=CCC2)cc1]

in a therapeutically effective amount for inhibiting activation of at least one muscarinic receptor selected from the group consisting of: $M_1$, $M_2$, $M_3$, $M_4$, and $M_5$ in a subject.

5. A composition comprising a pharmaceutically acceptable carrier and a bitopic muscarinic antagonist having the formula:

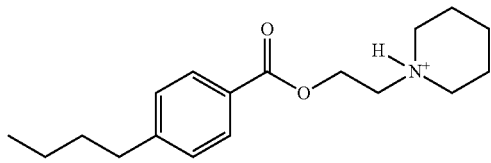 [SMILES: CCCCc1ccc(C(=O)OCC[NH+]2CCCCC2)cc1]

in a therapeutically effective amount for inhibiting activation of at least one muscarinic receptor selected from the group consisting of: $M_1$, $M_2$, $M_3$, $M_4$, and $M_5$ in a subject.

6. A composition comprising a pharmaceutically acceptable carrier and a bitopic muscarinic antagonist having the formula:

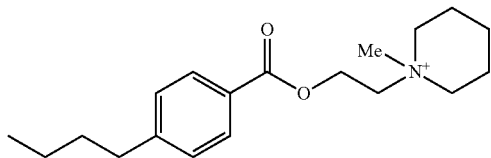 [SMILES: CCCCc1ccc(C(=O)OCC[N+]2(C)CCCCC2)cc1]

in a therapeutically effective amount for inhibiting activation of at least one muscarinic receptor selected from the group consisting of: $M_1$, $M_2$, $M_3$, $M_4$, and $M_5$ in a subject.

7. A kit for treating a disease or disorder associated with activity of a muscarinic receptor in a subject, the kit comprising:

(a) the composition of any one of claims 1, 2, 3, 4, 5 and 6, in a therapeutically effective amount for activating or inhibiting activity of at least one muscarinic receptor in the subject;

(b) instructions for use; and (c) packaging.

8. The kit of claim 7, wherein the at least one muscarinic receptor is selected from the group consisting of: $M_1$, $M_2$, $M_3$, $M_4$, and $M_5$.

9. The kit of claim 7, wherein the composition is formulated for oral or intravenous administration.

* * * * *